United States Patent
Marinangeli et al.

(12) 
(10) Patent No.: US 6,448,458 B1
(45) Date of Patent: Sep. 10, 2002

(54) ARYLALKANE COMPOSITIONS PRODUCED BY ISOMERIZATION, DEHYDROGENATION, AND ALKYLATION

(75) Inventors: Richard E. Marinangeli; R. Joe Lawson, both of Arlington Heights; Leonid B. Galperin, Wilmette; Thomas R. Fritsch, Villa Park, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/705,859

(22) Filed: Nov. 3, 2000

Related U.S. Application Data

(62) Division of application No. 09/356,574, filed on Jul. 19, 1999, now Pat. No. 6,187,981.

(51) Int. Cl.$^7$ .................. C07C 15/00; C07C 15/107
(52) U.S. Cl. ......................................... 585/24
(58) Field of Search ................... 585/24, 323, 448, 585/455, 740, 750, 751, 661, 660

(56) References Cited

U.S. PATENT DOCUMENTS

| | | | |
|---|---|---|---|
| 4,046,533 A | * 9/1977 | Olund ................. | 62/468 |
| 4,310,440 A | 1/1982 | Wilson et al. .......... | 252/435 |
| 4,440,871 A | 4/1984 | Lok et al. ............. | 502/214 |
| 4,758,419 A | 7/1988 | Lok et al. ............. | 423/306 |
| 4,793,984 A | 12/1988 | Lok et al. ............. | 423/306 |
| 4,943,424 A | 7/1990 | Miller ................. | 423/328 |
| 5,087,347 A | 2/1992 | Miller ................. | 208/46 |
| 5,158,665 A | 10/1992 | Miller ................. | 208/46 |
| 5,208,005 A | 5/1993 | Miller ................. | 423/702 |
| 5,246,566 A | 9/1993 | Miller ................. | 208/27 |
| 5,276,231 A | 1/1994 | Kocal et al. ........... | 585/323 |
| 6,111,158 A | * 8/2000 | Marinangeli et al. ..... | 585/467 |

FOREIGN PATENT DOCUMENTS

| WO | WO 99/05082 | 2/1999 |
|---|---|---|
| WO | WO 99/05084 | 2/1999 |
| WO | WO 99/05241 | 2/1999 |
| WO | WO 99/05243 | 2/1999 |
| WO | WO 99/07656 | 2/1999 |

OTHER PUBLICATIONS

*Handbook of Petroleum Refining Processes* edited by Robert A. Meyers, (McGraw-Hill, New York, $2^{nd}$ Ed., 1997), pp. 1.53 to 1.66 and pp. 5.11 to 5.19.

Article "New Molecular Sieve Process for Lube Dewaxing by Wax Isomerization" by S.J. Miller, *Microporous Materials* 2 (1994), pp. 439–449.

* cited by examiner

*Primary Examiner*—Thuan D. Dang
(74) *Attorney, Agent, or Firm*—John G. Tolomei; James C. Paschall; Michael A. Moore

(57) ABSTRACT

The present invention is a process for producing arylalkanes by paraffin isomerization followed by paraffin dehydrogenation and then by alkylation of an aryl compound by a lightly branched olefin. The effluent of the alkylation zone comprises paraffins that are recycled to the isomerization step or to the dehydrogenation step. This invention is also a process that that sulfonates phenyl-alkanes having lightly branched aliphatic alkyl groups that to produce modified alkylbenzene sulfonates. In addition, this invention is the compositions produced by these processes, which can be used as detergents having improved cleaning effectiveness in hard and/or cold water while also having biodegradability comparable to that of linear alkylbenzene sulfonates, as lubricants, and as lubricant additives. This invention is moreover the use of compositions produced by these processes as lubricants and lubricant additives.

32 Claims, 1 Drawing Sheet

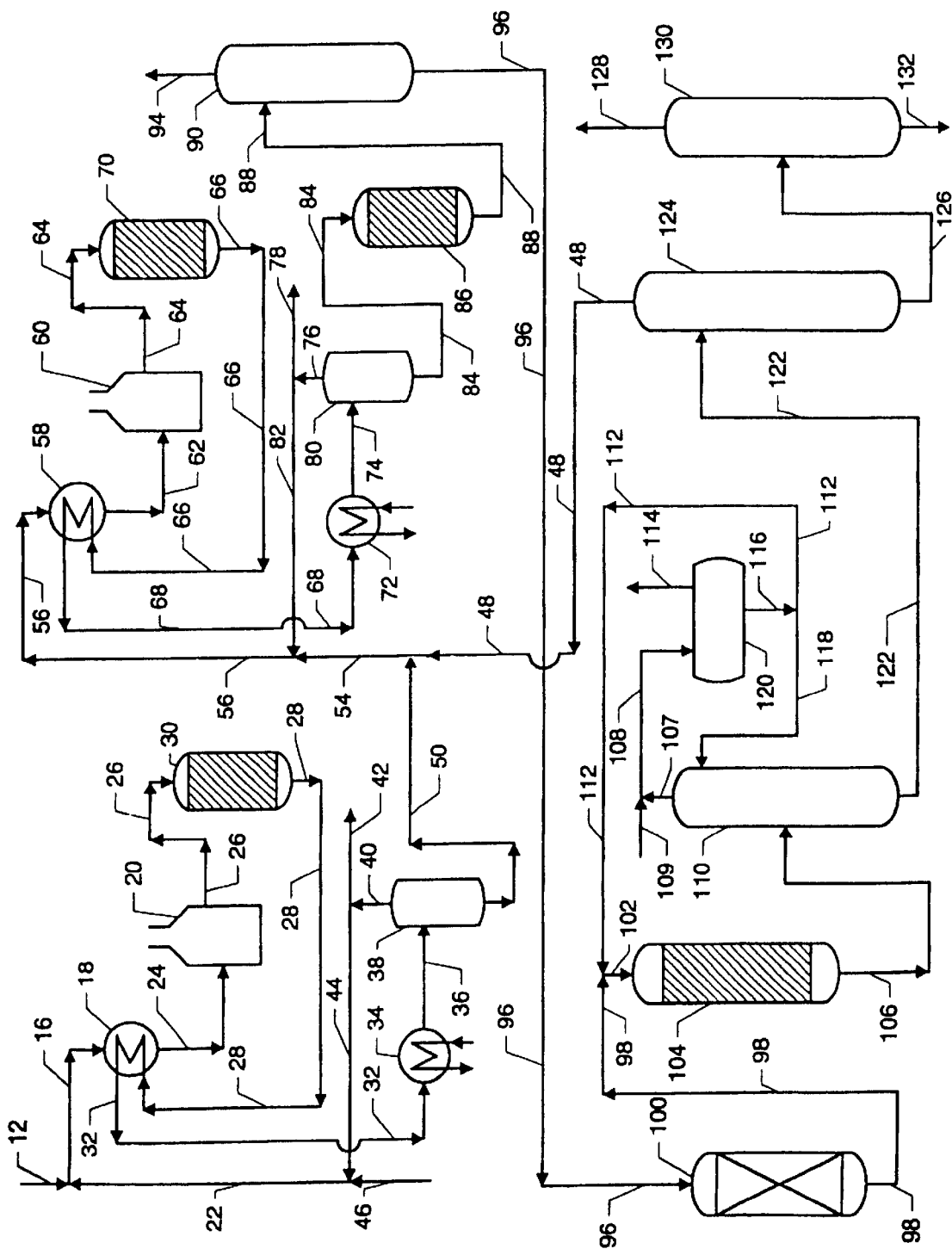

ARYLALKANE COMPOSITIONS PRODUCED BY ISOMERIZATION, DEHYDROGENATION, AND ALKYLATION

CROSS-REFERENCE TO RELATED APPLICATION

This application is a division of U.S. application Ser. No. 09/356,574 filed Jul. 19, 1999, now U.S. Pat. No. 6,187,981 the entire contents of which are hereby incorporated by reference.

FIELD OF THE INVENTION

The invention relates to a process for the selective production of arylalkane and arylalkane sulfonate compositions, to the particular arylalkane are arylalkane sulfonate compositions produced therefrom, and to uses of those compositions.

BACKGROUND OF THE INVENTION

More than thirty years ago, many household laundry detergents were made of branched alkylbenzene sulfonates (BABS). BABS are manufactured from a type of alkylbenzenes called branched alkylbenzenes (BAB). Alkylbenzenes (phenyl-alkanes) refers to a general category of compounds having an aliphatic alkyl group bound to a phenyl group and having the general formula of $(m_i\text{-alkyl}_i)_i\text{-n-phenyl-alkane}$. The aliphatic alkyl group consists of an aliphatic alkyl chain, which is referred to by "alkane" in the $(m_i\text{-alkyl}_i)_i\text{-n-phenyl-alkane}$ formula. Of the chains of the aliphatic alkyl group, the aliphatic alkyl chain is the longest straight chain that has a carbon bound to the phenyl group. The aliphatic alkyl group may also consist of one or more alkyl group branches, each of which is attached to the aliphatic alkyl chain and is designated by a corresponding "$(m_i\text{-alkyl}_i)$" in the $(m_i\text{-alkyl}_i)_i\text{-n-phenyl-alkane}$ formula. If it is possible to select two or more chains of equal lengths as the aliphatic alkyl chain, the choice goes to the chain carrying the greatest number of alkyl group branches. The subscript counter "i" thus has a value of from 1 to the number of alkyl group branches, and for each value of i, the corresponding alkyl group branch is attached to carbon number $m_i$ of the aliphatic alkyl chain. The phenyl group is attached to the aliphatic alkyl group, specifically to carbon number n of the aliphatic alkyl chain. The aliphatic alkylation chain is numbered from one end to the other, the direction being chosen so as to give the lowest number possible to the position of the phenyl group.

The standard process used by the petrochemical industry for producing BAB consists of oligomerizing light olefins, particularly propylene, to branched olefins having 10 to 14 carbon atoms and then alkylating benzene with the branched olefins in the presence of a catalyst such as HF. Although the product BAB comprises a large number of alkyl-phenyl-alkanes having the general formula $(m_i\text{-alkyl}_i)_i\text{-n-phenyl-alkane}$, for the purpose of illustrating three important characteristics of BAB it is sufficient to point out only two examples of BAB: m-alkyl-m-alkyl-n-phenyl-alkanes where $m \neq n$, and m-alkyl-m-phenyl-alkanes where $m \geq 2$.

The most prominent characteristic of BAB is that, for a large proportion of BAB, there is attached to the aliphatic alkyl chain of BAB generally at least one alkyl group branch, and more commonly three or more alkyl group branches. BAB thus has a relatively large number of primary carbon atoms per aliphatic alkyl group, since the number of primary carbon atoms per aliphatic alkyl group in BAB equals the number of alkyl group branches per aliphatic alkyl group plus either one if n=1, or two if $n \geq 2$, provided that the alkyl group branches themselves are unbranched. If any alkyl group branch itself is branched, then the aliphatic alkyl group in BAB has even more primary carbon atoms. Thus the aliphatic alkyl group in BAB usually has three, four, or more primary carbon atoms. As for the alkyl group branches of the aliphatic alkylation group in BAB, each alkyl group branch is usually a methyl group branch, although ethyl, propyl, or higher alkyl group branches are possible.

Another characteristic of BAB is that the phenyl group in BAB can be attached to any non-primary carbon atom of the aliphatic alkyl chain. This is typical of BAB that is produced from the standard BAB process used by the petrochemical industry. Except for 1-phenyl-alkanes whose formation is known to be disfavored due to the relative instability of the primary carbenium ion and neglecting the relatively minor effect of the branches of the branched paraffins, the oligomerization step produces a carbon-carbon double bond that is randomly distributed along the length of the aliphatic alkyl chain, and the alkylation step nearly randomly attaches the phenyl group to a carbon along the aliphatic alkyl chain. Thus, for example, for a phenyl-alkane which has an aliphatic alkyl chain having 10 carbon atoms and which was produced by the standard BAB process, the phenyl-alkane product would be expected to be an approximately random distribution of 2-, 3-, 4-, and 5-phenyl-alkanes, and the selectivity of the process to a phenyl-alkane like 2-phenyl alkane would be 25 if the distribution was perfectly random, but is typically between about 10 and about 40.

A third characteristic of BAB is the relatively high probability that one of the carbons of the aliphatic alkyl group is a quaternary carbon. In BAB, the quaternary carbon may be, as illustrated by the first BAB example, a carbon in the aliphatic alkyl group other than the carbon that is bonded by a carbon-carbon bond to a carbon in the phenyl group. However, as is illustrated by the BAB second example, the quaternary carbon may also be the carbon that is bonded by a carbon-carbon bond to a carbon in the phenyl group. When a carbon atom on the alkyl side chain not only is attached to two other carbons on the alkyl side chain and to a carbon atom of an alkyl group branch but also is attached to a carbon atom of the phenyl group, the resulting alkyl-phenyl-alkane is referred to as a "quaternary alkyl-phenyl-alkane" or simply a "quat." Thus, quats comprise alkyl-phenyl-alkanes having the general formula m-alkyl-m-phenyl-alkane. If the quaternary carbon is the second carbon atom numbered from an end of the alkyl side chain, the resulting 2-alkyl-2-phenyl-alkane is referred to as an "end quat.", If the quaternary carbon is any other carbon atom of the alkyl side chain, as in the second BAB example, then the resulting alkyl-phenyl-alkane is referred to as "internal quat." In known processes for producing BAB, a relatively high proportion, typically greater than 10 mol-%, of the BAB is internal quats.

About thirty years ago it became apparent that household laundry detergents made of BABS were gradually polluting rivers and lakes. Investigation into the problem led to the recognition that BABS were slow to biodegrade. Solution of the problem led to the manufacture of detergents made of linear alkylbenzene sulfonates (LABS), which were found to biodegrade more rapidly than BABS. Today, detergents made of LABS are manufactured worldwide. LABS are manufactured from another type of alkylbenzenes called linear alkylbenzenes (LAB). The standard process used by the petrochemical industry for producing LAB consists of dehydrogenating linear paraffins to linear olefins and then alkylating benzene with the linear olefins in the presence of a catalyst such as HF or a solid catalyst. LAB are phenyl-alkanes comprising a linear aliphatic alkyl group and a phenyl group and have the general formula n-phenyl-alkane. LAB has no alkyl group branches, and consequently the linear aliphatic alkyl group normally has two primary carbon atoms (i.e., $n \geq 2$). Another characteristic of LAB that is produced by the standard LAB process is that the phenyl group in LAB is usually attached to any secondary carbon atom of the linear aliphatic alkyl group. In LAB produced using HF catalyst the phenyl group is slightly more likely to attach to a secondary carbon near the center as opposed to near the end of the linear aliphatic alkyl group, while in LAB produced by the Detal™ process approximately 25–35 mol-% of n-phenyl-alkanes are 2-phenyl-alkanes.

Over the last few years, other research has identified certain modified alkylbenzene sulfonates, which are referred to herein as MABS, which are different in composition from all alkylbenzene sulfonates used currently in commerce, including BABS and LABS, and from all alkylbenzene sulfonates produced by prior alkylbenzene processes, including those which alkylate aromatics using catalysts such as HF, aluminum chloride, silica-alumina, fluorided silica-alumina, zeolites, and fluorided zeolites. MABS also differ from these other alkylbenzene sulfonates by having improved laundry cleaning performance, hard surface cleaning performance, and excellent efficiency in hard and/or cold water, while also having biodegradability comparable to that of LABS.

MABS can be produced by sulfonating a third type of alkylbenzenes called modified alkylbenzenes (MAB), and the desired characteristics of MAB are determined by the desired solubility, surfactancy, and biodegradability properties of MABS. MAB is a phenyl-alkane comprising a lightly branched aliphatic alkyl group and a phenyl group and has the general formula $(m_i\text{-alkyl}_i)_i$-n-phenyl-alkane. MAB usually has only one alkyl group branch, and the alkyl group branch is a methyl group, which is preferred, an ethyl group, or an n-propyl group, so that, where there is only one alkyl group branch and $n \neq 1$, the aliphatic alkyl group in MAB has three primary carbons. However, the aliphatic alkyl group in MAB may have two primary carbon atoms if there is only one alkyl group branch and $n=1$, or, if there are two alkyl group branches and $n \neq 1$, four primary carbons. Thus, the first characteristic of MAB is that the number of primary carbons in the aliphatic alkyl group in MAB is intermediate between that in BAB and that in LAB. Another characteristic of MAB is that it contains a high proportion of 2-phenyl-alkanes, namely that from about 40 to about 100% of phenyl groups are attached selectively to the second carbon atom as numbered from an end of the alkyl side chain.

A final characteristic of the MAB alkylate is that the MAB has a relatively low proportion of internal quats. Some internal quats such as 5-methyl-5-phenyl-undecane produce MABS that has shown slower biodegradation, but end quats such as 2-methyl-2-phenyl-undecane produce MABS that show biodegradation similar to that of LABS. For example, biodegradation experiments show that in a porous pot activated sludge treatment, the ultimate biodegradation was greater for sodium 2-methyl-2-undecyl [$C^{14}$] benzene-sulfonate than for sodium 5-methyl-5-undecyl [$C^{14}$] benzenesulfonate. See the article entitled "Biodegradation of Coproducts of Commercial Linear Alkylbenzene Sulfonate," by A. M. Nielsen et al., in Environmental Science and Technology, Vol. 31, No. 12, 3397–3404 (1997). A relatively low proportion, typically less than 10 mol-%, of MAB is is internal quats.

Because of the advantages of MABS over other alkylbenzene sulfonates, catalysts and processes are sought that selectively produce MAB. As suggested by the foregoing, two of the chief criteria for an alkylation process for the production of MAB are selectivity to 2-phenyl-alkanes and selectivity away from internal quaternary phenyl-alkanes. Prior art alkylation processes for the production of LAB using catalysts such as aluminum chloride or HF are incapable of producing MAB having the desired 2-phenyl-alkane selectivity and internal quat selectivity. In these prior art processes, when lightly branched olefins (i.e., olefins that have essentially the same light branching as that of the aliphatic alkyl group of MAB) react with benzene, quaternary phenyl-alkanes selectively form. One reaction mechanism that accounts for such selective quaternary phenyl-alkane formation is that the delinearized olefins convert, to various extents, into primary, secondary, and tertiary carbenium ion intermediates. Of these three carbenium ions, tertiary carbenium ions are the most stable, and because of their stability, are the most likely to form and react with benzene, thus forming a quaternary phenyl-alkane.

One process that has been proposed for producing MAB comprises a three-step process. First, a feedstock comprising paraffins is passed to an isomerization zone to isomerize the paraffins and to produce an isomerized product stream comprising lightly branched paraffins (i.e., paraffins that have essentially the same light branching as that of the aliphatic alkyl group of MAB). Next, the isomerized product stream passes to a dehydrogenation zone where the lightly branched paraffins are dehydrogenated to produce a dehydrogenated product stream comprising lightly branched monoolefins (i.e., monoolefins that have essentially the same light branching as that of the lightly branched paraffins, and, consequently, that of the aliphatic alkyl group of MAB). Finally, the dehydrogenated product stream passes to an alkylation zone where the lightly branched monoolefins in the dehydrogenated product stream react with benzene to form MAB.

One of the problems with this proposed process is that conventional dehydrogenation reaction zones typically convert only about 10 wt-% of the entering paraffins to olefins, so that usually about 90 wt-% of the product stream from the dehydrogenation zone comprises paraffins, including both linear and nonlinear paraffins. Because the product stream from the dehydrogenation zone enters the alkylation zone, these paraffins all enter the alkylation zone as well. Although it would be desirable to remove the paraffins prior to entering the alkylation zone, the difficulty of separating these paraffins from the monoolefins all of the same carbon number precludes such an arrangement. In the alkylation zone, typically more than 90 wt-% of the entering monoolefins are converted to phenyl-alkanes while the entering paraffins are essentially inert or unreactive. Thus, the alkylation effluent contains not only the desired product MAB but also these paraffins. Accordingly, processes for the production of MAB are sought that efficiently recover and utilize paraffins in the alkylation effluent.

SUMMARY OF THE INVENTION

In one aspect, this invention is a process for the production of arylalkanes, in particular modified alkylbenzenes (MAB), by the steps of paraffin isomerization, paraffin dehydrogenation, and alkylation of an aryl compound, in which paraffins in the alkylation effluent are recycled to the isomerization step and/or the dehydrogenation step. The paraffins that are recycled may be linear or nonlinear paraffins, including lightly branched paraffins. Because the recycled paraffins can be converted into lightly branched olefins, this invention efficiently recovers paraffins in the alkylation effluent and uses them to produce valuable arylalkane products. This aspect of the invention thus increases the yield of valuable products for a given amount of paraffinic feedstock charged to the process while avoiding the difficulty of separating the paraffins from the monoolefins after the paraffin dehydrogenation step and prior to the alkylation step.

The process aspect of this invention has several objectives. The primary objective of this invention is to produce arylalkanes, in particular modified alkylbenzenes (MAB) by paraffin isomerization followed by paraffin dehydrogenation to olefins and then by alkylation of aromatics by olefins. An additional objective of this invention is to increase the yield of arylalkane in such a process and thereby to decrease the amount of paraffin feedstock, which is required for the process. Yet another objective is to remove unreacted paraffins from the arylalkane product without the need for a difficult and/or costly separation of paraffins from olefins after the dehydrogenation step and prior to the alkylation step.

This invention, when used for detergent alkylation, produces detergents that meet the increasingly stringent requirements of 2-phenyl-alkanes selectivity and internal quaternary phenyl-alkane selectivity for the production of modified alkylbenzenes (MAB). Thus, in another aspect of this invention, the MAB, in turn, can be sulfonated to produce modified linear alkylbenzene sulfonates (MABS), which have improved cleaning effectiveness in hard and/or cold water while also having biodegradability comparable to that of linear alkylbenzene sulfonates.

In yet other aspect, this invention is the MAB and MABS compositions produced by the processes of this invention. It is believed that the MAB and MABS produced by the processes of this invention are not necessarily the products that would be produced by the prior art processes that do not recycle paraffins. Without being bound to any particular theory, it is believed that in the dehydrogenation zone the extent of conversion of branched paraffins can be greater than that of normal (linear) paraffins, and/or that the extent of conversion of heavier paraffins can be greater than that of lighter paraffins. In these cases, the concentration of linear paraffins and/or lighter paraffins in the recycle paraffin stream could increase. This, in turn, could increase the concentration and ultimately the conversion of linear and/or lighter paraffins in the dehydrogenation zone until the rate of removal from the process of linear and/or lighter paraffins via dehydrogenation and subsequent alkylation equals the rate of introduction into the dehydrogenation zone of those paraffins from the paraffin isomerization zone. Accordingly, for a given extent of olefin conversion in the alkylation zone, the aliphatic alkyl chain of the MAB product of the present invention can be less branched and/or shorter than that of the prior art processes. On sulfonation, the MABS product of the present invention could likewise tend to have a less branched and/or shorter aliphatic alkyl chain than that of the prior art processes. Thus, for a given combination of feedstocks, the processes of this invention could produce particular MAB and MABS products having aliphatic alkyl chain with specially tailored extents of branching that are not necessarily the same as those of the prior art processes.

This invention is, in another of its aspects, the use of MAB and MABS produced by the process of this invention as a lubricant and as a lubricant additive, respectively.

Additional aspects and embodiments are described in the following description of this invention.

INFORMATION DISCLOSURE

LAB processes are described in the book edited by Robert A. Meyers entitled *Handbook of Petroleum Refining Processes*, (McGraw-Hill, NewYork, Second Edition, 1997) at pages 1.53 to 1.66, the teachings of which are incorporated herein by reference. Paraffin dehydrogenation processes are described in the Meyers book at pages 5.11 to 5.19, the teachings of which are incorporated herein by reference.

PCT International Publication Nos. WO 99/05082, WO 99/05084, 99/05241, and WO 99/05243, all four of which were published on Feb. 4, 1999, and which are incorporated herein by reference, disclose alkylation processes for uniquely lightly branched or delinearized alkylbenzenes. PCT International Publication No. WO99/07656, published on Feb. 18, 1999, which is incorporated herein by reference, discloses processes for such alkylbenzenes using adsorptive separation.

U.S. Patent No. 5,276,231 (Kocal et al.) describes a process for the production of linear alkylaromatics with selective removal of aromatic by-products of the paraffin dehydrogenation zone of the process. In U.S. Pat. No. 20 5,276,231, paraffins from the paraffin column of the alkylation zone are recycled to the reactor of the dehydrogenation zone, with or without selective hydrogenation of any monoolefins in the paraffin recycle stream. U.S. Pat. No. 5,276,231 also teaches the selective hydrogenation of diolefinic by-products from the dehydrogenation zone. The teachings of U.S. Pat. No. 5,276,231, are incorporated herein by reference.

Isomerization of paraffins using crystalline, microporous aluminophosphate compositions is described in U.S. Pat. No. 4,310,440. The use of crystalline microporous silicoaluminophosphates to isomerize paraffins is described in U.S. Pat. No. 4,440,871. Paraffins can also be isomerized using crystalline molecular sieves having three-dimensional microporous framework structures of $MgO_2$, $AlO_2$, $PO_2$, and $SiO_2$ tetrahedral units, as described in U.S. Pat. No. 4,758,419. U.S. Pat. No. 4,793,984 describes isomerization of paraffins using crystalline molecular sieves having three-dimensional microporous framework structures of $ElO_2$, $AlO_2$, $PO_2$, and $SiO_2$ tetrahedral units, where El includes but is not limited to arsenic, beryllium, boron, chromium, cobalt, gallium germanium, iron, lithium, magnesium, manganese, titanium, vanadium, and zinc. European Patent Application EP-640,576 describes isomerizing a gasoline boiling range feedstock comprising linear paraffins using a MeAPO and/or MeAPSO medium-pore molecular sieve and at least one Group VIII metal component, wherein Me is at least Mg, Mn, Co, or Zn.

U.S. Pat. No. 5,246,566 (Miller) and the article in Microporous Materials 2 (1994) 439–449, describe lube dewaxing by wax isomerization using molecular sieves.

U.S. Pat. Nos. 4,943,424; 5,087,347; 5,158,665; and 5,208,005 teach using a crystalline silicoaluminophosphate, SM-3, to dewax hydrocarbonaceous feeds. U.S. Pat. Nos. 5,158,665 and 5,208,005 also teach using SM-3 to isomerize a waxy feedstock.

DETAILED DESCRIPTION OF THE INVENTION

Two feedstocks consumed in the subject process are a paraffinic compound and an aryl compound. The paraffinic feedstock preferably comprises nonbranched (linear) or normal paraffin molecules having a total number of carbon atoms per paraffin molecule of generally from about 8 to about 28, preferably from 8 to 15, and more preferably from 10 to 15 carbon atoms. Two carbon atoms per nonbranched paraffin molecule are primary carbon atoms and the remaining carbon atoms are secondary carbon atoms. A secondary carbon atom is a carbon atom which, although possibly bonded also to other atoms besides carbon, is bonded to only two carbon atoms.

In addition to nonbranched paraffins, other acyclic compounds may be charged to the subject process. These other acyclic compounds may be charged to the subject process either in the paraffinic feedstock containing nonbranched paraffins, or via one or more other streams that are charged to the subject process. One such acyclic compound is a lightly branched: paraffin, which as used herein, refers to a paraffin having a total number of carbon atoms of from about 8 to about 28, of which three or four of the carbon atoms are primary carbon atoms and none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms. Preferably, the lightly branched paraffin has a total number of from 8 to carbon atoms, and more preferably from 10 to 15 carbon atoms. The lightly branched paraffin generally comprises an aliphatic alkane having the general formula of $(p_i\text{-alkyl}_i)_i$-alkane. The lightly branched paraffin consists of an aliphatic alkyl chain, which is referred to by "alkane" in the $(p_i\text{-alkyl}_i)_i$-alkane formula, and is the longest straight chain of the lightly branched paraffin. The lightly branched monoolefin also consists of one or more alkyl group branches, each of which is attached to the aliphatic alkyl chain and is designated by a corresponding "$(p_i\text{-alkyl}_i)_i$" in the $(p_i\text{-alkyl}_i)_i$-alkane formula. If it is possible to select two or more chains of equal lengths as the aliphatic alkyl chain, the choice goes to the chain carrying the greatest number of alkyl group branches. The subscript counter "i", thus has a value of from 1 to the number of alkyl group branches, and for each value of i, the corresponding alkyl group branch is attached to carbon number $p_i$ of the aliphatic alkyl chain. The aliphatic alkyl chain is numbered from one end to the other, the direction being chosen so as to give the lowest numbers possible to the carbon atoms having alkyl group branches.

The alkyl group branch or branches of the lightly branched paraffin are generally selected from methyl, ethyl, and propyl groups, with shorter and normal branches being preferred. Preferably, the lightly branched paraffin has only one alkyl group branch, but two alkyl group branches are also possible. Lightly branched paraffins having either two alkyl group branches or four primary carbon atoms comprise generally less than 40 mol-%, and preferably less than about is 25 mol-%, of the total lightly branched paraffins. Lightly branched paraffins having either one alkyl group branch or three primary carbon atoms comprise preferably more than 70 mol-% of the total lightly branched monoolefins. Any alkyl group branch can be bonded to any carbon on the aliphatic alkyl chain.

Other acyclic compounds that may be charged to the subject process are paraffins that are more highly branched than the lightly branched paraffins. However, on dehydrogenation such highly branched paraffins tend to form highly branched monoolefins which on alkylation tend to form BAB. For example, paraffin molecules consisting of at least one quaternary carbon atom tend on dehydrogenation followed by alkylation to form phenyl-alkanes that have in the aliphatic alkyl portion a quaternary carbon atom that is not bonded by a carbon-carbon bond with a carbon atom of the aryl portion. Therefore, the quantity of these highly branched paraffins charged to the process is preferably minimized. Paraffin molecules consisting of at least one quaternary carbon atom generally comprise less than 10 mol-%, preferably less than 5 mol-%, more preferably less than 2 mol-%, and most preferably less than 1 mol-% of the paraffinic feedstock or of the sum of all the paraffins that are charged to the subject process.

The paraffinic feedstock is normally a mixture of linear and lightly branched paraffins having different carbon numbers. The production of the paraffinic feedstock is not an essential element of this invention, and any suitable method for producing the paraffinic feedstock may be used. A preferred method for the production of the paraffinic feedstock is the separation of nonbranched (linear) hydrocarbons or lightly branched hydrocarbons from a kerosene boiling range petroleum fraction. Several known processes that accomplish such a separation are known. One process, the UOP MoleX™ process, is an established, commercially proven method for the liquid-phase adsorption separation of normal paraffins from isoparaffins and cycloparaffins using the UOP Sorbex separation technology. See Chapters 10.3 and 10.7 in the book entitled *Handbook of Petroleum Refining Process*, Second Edition, edited by Robert A. Meyers, published by McGraw-Hill, New York, 1997. Another suitable, established, and proven process is the UOP Kerosene Isosiv™ Process, which employs vapor-phase adsorption for separating normal paraffins from nonnormal paraffins using molecular sieves in an adsorber vessel. See Chapter 10.6 in the above-mentioned Meyers book. Another vapor-phase adsorption process, which uses ammonia as the desorbent, is described in the paper entitled "Exxon Chemical's Normal Paraffins Technologies," written by R. A. Britton, which was prepared for presentation at the AlChE Annual 1991 National Meeting, Design of Adsorption Systems Session, Los Angeles, California, Nov. 21, 1991, and in the article written by W. J. Asher et al. and starting at page 134 of Hydrocarbon Processing, Vol. 48, No. 1 (January 1969). Chapter 11 of the book entitled *Principles of Adsorption and Adsorption Processes*, by Douglas M. Ruthven, published by John Wiley and Sons, New York, 1984, describes other adsorption separation processes. The feed streams to these above-mentioned separation processes, which comprise branched paraffins that are more highly branched than the lightly branched paraffins, can be obtained by extraction or by suitable oligomerization processes. However, the above-mentioned adsorption separation processes are not necessarily equivalent in terms of acceptable concentrations of impurities such as sulfur in their respective feed streams.

The composition of a mixture of linear, lightly branched, and branched paraffins, such as that of the paraffinic feedstock or of the feed stream to the above-mentioned adsorption separation processes, can be determined by analytical methods that are well-known to a person of ordinary skill in the art of gas chromatography and need not be described here in detail. The article written by H. Schulz, et al. and published starting at page 315 of the Chromatographia 1, 1968, which is incorporated herein by reference, describes a temperature-programmed gas chromatograph apparatus and method that is suitable for identifying components in complex mixtures of paraffins. A person of ordinary skill in the art can separate and identify the components in a mixture of paraffins using essentially the apparatus and method described in the article by Schulz et al.

The aryl feedstock comprises an aryl compound, which is benzene when the process is detergent alkylation. In a more general case, the aryl compound of the aryl feedstock may be alkylated or otherwise substituted derivatives or of a higher molecular weight than benzene, including toluene, ethylbenzene, xylene, phenol, naphthalene, etc., but the product of such an alkylation may not be as suitable a detergent precursor as alkylated benzenes.

For purposes of discussion, the subject process may be divided into an isomerization section, a dehydrogenation section, and an alkylation section. In the isomerization section, the paraffinic feedstock is passed to a skeletal isomerization zone, which decreases the linearity and adjusts the number of primary carbon atoms of the paraffin molecules in the paraffinic feedstock. By "skeletal isomerization" of a paraffin molecule, it is meant isomerization that increases the number of primary carbon atoms of the paraffin molecule. The skeletal isomerization of the paraffin molecule preferably comprises increasing by 2, or more preferably by 1, the number of methyl group branches of the aliphatic alkyl chain. Because the total number of carbon atoms of the paraffin molecule remains the same, each additional methyl group branch causes a corresponding reduction by one of the number of carbon atoms in the aliphatic alkyl chain.

The isomerization section will preferably be configured substantially in the manner shown in the drawing. In this arrangement, a feedstream containing paraffins combines with recycled hydrogen. This forms an isomerization reactant stream which is heated and passed through a bed of a suitable catalyst maintained at the proper isomerization conditions of temperature, pressure, etc. The effluent of this catalyst bed, or isomerization reactor effluent stream, is cooled, partially condensed, and passed to a vapor-liquid, or product, separator. The condensed material withdrawn from the product separator may be passed to a stripping separation zone which includes a stripping column that removes all compounds which are more volatile than the lightest aliphatic hydrocarbon which is desired to charge to the dehydrogenation section of the process. Alternatively, the condensed material may be passed without stripping and with its more volatile aliphatic hydrocarbons to the dehydrogenation section of the process, and in this case a stripping separation zone is provided for the dehydrogenated product stream in order to remove all compounds which are more volatile than the lightest aliphatic hydrocarbon which it is desired to charge to the alkylation section of the process. This latter alternative will be described in greater detail hereinafter. In either case, the paraffin-containing net stream that passes from the isomerization section to the dehydrogenation section of the process is referred to herein as the isomerized product stream.

Skeletal isomerization of the paraffinic feedstock can be accomplished in any manner known in the art or by using any suitable catalyst known in the art. Suitable catalysts comprise a metal of Group VIII (IUPAC 8-10) of the Periodic Table and a support material. Suitable Group VIII metals include platinum and palladium, each of which may be used alone or in combination. The support material may be amorphous or crystalline. Suitable support materials include amorphous alumina, amorphous silica-alumina, ferrierite, ALPO-31, SAPO-11, SAPO-31, SAPO-37, SAPO41, SM-3, and MgAPSO-31, each of which may be used alone or in combination. ALPO-31 is described in U.S. Pat. No. 4,310,440 (Wilson et al.). SAPO-11, SAPO-31, SAPO-37, and SAPO41 are described in U.S. Pat. No. 4,440,871 (Lok et al.). SM-3 is described in U.S. Pat. Nos. 4,943,424 (Miller); 5,087,347 (Miller); 5,158,665 (Miller); and 5,208,005 (Miller). MgAPSO is a MeAPSO, which is an acronym for a metal aluminumsilicophosphate molecular sieve, where the metal Me is magnesium (Mg). MeAPSOs are described in U.S. Pat. No. 4,793,984 (Lok et al.), and MgAPSOs are described in U.S. Pat. No. 4,758,419 (Lok et al.). MgAPSO-31 is a preferred MgAPSO, where 31 means a MgAPSO having structure type 31. The isomerization catalyst may also comprise a modifier selected from the group consisting of lanthanum, cerium, praseodymium, neodymium, samarium, gadolinium, terbium , and mixtures thereof, as described in U.S. Pat. Nos. 5,716,897 (Galperin et al.) and 5,851,949 (Galperin et al.). It is believed that other suitable support materials include ZSM-22, ZSM-23, and ZSM-35, which are described for use in dewaxing in U.S. Pat. No. 5,246,566 (Miller) and in the article entitled "New molecular sieve process for lube dewaxing by wax isomerization," written by S. J. Miller, in Microporous Materials 2 (1994) 439–449. The teachings of U.S. Pat. Nos. 4,310,440; 4,440,871; 4,793,984; 4,758,419; 4,943,424; 5,087,347; 5,158,665; 5,208,005; 5,246,566; 5,716,897; and 5,851,949 are incorporated herein by reference thereto.

Operating conditions for skeletal isomerization of the paraffinic feedstock include vapor phase, liquid phase, and a combination of vapor and liquid phases. The hydrocarbons that contact the skeletal isomerization catalyst may be in the vapor phase but are preferably in the liquid phase. The hydrocarbons contact a solid catalyst in the presence of hydrogen. Although all of the hydrogen may be soluble in the liquid hydrocarbons, hydrogen in excess of that soluble may also be present. The configuration of the isomerization reaction zone may comprise a trickle-bed reactor, in which the paraffinic feedstock is allowed to trickle as a liquid through a fixed bed of solid catalyst in the presence of hydrogen vapor. The isomerization conditions include a temperature of generally from about 50 to about 400° F. (122 to 752° C.). The isomerization pressure is generally in the range of from atmospheric pressure to about 2000 psi(g) (13790 kPa(g)), but usually the pressure in the isomerization zone is maintained as low as practicable, to minimize capital and operating costs. The molar ratio of hydrogen per hydrocarbon is generally greater than 0.01:1, but is usually not more than 10:1.

The isomerized product stream comprises paraffins having a total number Is of carbon atoms per paraffin molecule of generally from about 8 to about 28, preferably from 8 to 15, and more preferably from 10 to 15 carbon atoms. The isomerized product stream generally contains a higher concentration of lightly branched paraffins, based on the total paraffins in the isomerized product stream, than the concentration of lightly branched paraffins in the paraffinic feedstock, based on the total paraffins in the paraffinic feedstock. The lightly branched paraffins having either two alkyl group branches or four primary carbon atoms comprise preferably less than 40 mol-%, and more preferably less than about 30 mol-%, of the total lightly branched paraffins in the isomerized product stream or in that portion of the isomerized product stream that passes to the dehydrogenation zone of the process. The lightly branched paraffins having either one alkyl group branch or three primary carbon atoms comprise preferably more than 70 mol-% of the total lightly branched paraffins in the isomerized product stream or in the portion of the isomerized product stream charged to the dehydrogenation zone. The lightly branched paraffins having 3 or 4 primary carbon atoms and no quaternary carbon atoms comprise preferably more than 25 mol-%, and more preferably more than 60 mol-%, of the isomerized product stream or in that portion of the isomerized product stream that passes to the dehydrogenation zone. Lightly branched paraffins having only one alkyl group branch and where the sole alkyl group branch is a methyl group are referred to herein as monomethyl-alkanes and are a preferred component of the isomerized product stream. Any alkyl group branch can be bonded to any carbon on the aliphatic alkyl chain. When present in the isomerized product stream with the lightly branched paraffins, the linear paraffin content may be as high as, or no more than, about 75 mol-% of the total paraffins but is generally less than about 40 mol-%, of the total paraffins in the isomerized product stream or in that portion of the isomerized product stream that is charged to the dehydrogenation zone.

Paraffin molecules consisting of at least one quaternary carbon atom generally comprise less than 10 mol-%, preferably less than 5 mol-%, more preferably less than 2 mol-%, and most preferably less than 1 mol-%, of the isomerized product stream or of that portion of the isomerized product stream that passes to the dehydrogenation zone.

The dehydrogenation section may be configured substantially in the manner shown in the drawing. Briefly, a stream containing paraffins combines with recycled hydrogen to form a dehydrogenation reactant stream that is heated and contacted with a dehydrogenation catalyst in a fixed bed maintained at dehydrogenation conditions. The effluent of the fixed catalyst bed, which is referred to herein as the dehydrogenation reactor effluent stream, is cooled, partially condensed, and passed to a vapor-liquid separator. The vapor-liquid separator produces a hydrogen-rich vapor phase and a hydrocarbon-rich liquid phase. The condensed liquid phase recovered from the separator passes to a stripping column, which removes all compounds which are more volatile than the lightest hydrocarbon which is desired to be passed to the alkylation section. The olefin-containing net stream that passes from the dehydrogenation section to the alkylation section of the process is referred to herein as the dehydrogenated product stream.

This invention is not limited to any one particular flow scheme for the dehydrogenation section, since dehydrogenation flow schemes other than that shown in the drawing are also within the scope of this invention as set forth in the claims. For example, the dehydrogenation catalyst may be in a moving catalyst bed or a fluidized bed. The dehydrogenation zone may comprise one or more catalyst-containing reaction zones with heat exchangers there between to ensure that the desired reaction temperature is maintained at the entrance to each reaction zone. One or more hot hydrogen-rich gas streams may be introduced between a first and a second reaction zone to increase the temperature of a stream passing from the first to the second reaction zone, as disclosed in U.S. Pat. Nos. 5,491,275 (Vora et al.) and 5,689,029 (Vora et al.), both of whose teachings are incorporated herein by reference thereto. Each reaction zone may be operated in a continuous-type or batch-type manner. for continuous or batch system. Each reaction zone may contain one or more catalyst beds. Hydrocarbons may contact any catalyst bed in an upward-, downward-, or radial-flow fashion. In a particularly compact and efficient arrangement, the contacting of the catalyst with hydrocarbons and heat exchanging may be accomplished in a heat exchanging reactor. One example of such a reactor is an isothermal reactor design using interleaved layers of plate heat exchange elements, which is described in U.S. Pat. No. 5,405,586 (Koves) which is incorporated herein by reference thereto. Another example of a reactor arrangement is disclosed in U.S. Pat. No. 5,525,311 (Girod et al.), where a reactant stream indirectly contacts a heat exchange stream and where an arrangement of corrugated heat exchange plates is used to control temperature conditions by varying the number and/or the arrangement of the corrugations along the plates. The teachings of U.S. Pat. No. 5,525,311 are incorporated herein by reference thereto.

Dehydrogenation catalysts are well known in the prior art as exemplified by U.S. Pat. Nos. 3,274,287; 3,315,007; 3,315,008; 3,745,112; 4,430,517; 4,716,143; 4,762,960; 4,786,625; and 4,827,072. It is believed that the choice of a particular dehydrogenation catalyst is not critical to the success of this invention. However, a preferred catalyst is a layered composition comprising an inner core and an outer layer bonded to the inner core, where the outer layer comprises a refractory inorganic oxide having uniformly dispersed thereon at least one platinum group (Group VIII (IUPAC 8-10)) metal and at least one promoter metal, and where at least one modifier metal is dispersed on the catalyst composition. Preferably, the outer layer is bonded to the inner core to the extent that the attrition loss is less than 10 wt-% based on the weight of the outer layer.

The preferred catalyst composition comprises an inner core composed of a material which has substantially lower adsorptive capacity for catalytic metal precursors, relative to the outer layer. Some of the inner core materials are also not substantially penetrated by liquids, e.g., metals. Examples of the inner core material include, but are not limited to, refractory inorganic oxides, silicon carbide, and metals. Examples of refractory inorganic oxides include without limitation alpha alumina, theta alumina, cordierite, zirconia, titania, and mixtures thereof. Preferred inorganic oxides are alpha alumina and cordierite.

These materials which form the inner core can be formed into a variety of shapes such as pellets, extrudates, spheres, or irregularly shaped particles, although not all materials can be formed into each shape. Preparation of the inner core can be done by means known in the art such as oil dropping, pressure molding, metal forming, pelletizing, granulation, extrusion, rolling methods, and marumerizing. A spherical inner core is preferred. The inner core whether spherical or not has an effective diameter of about 0.05 mm (0.0020 in) to about 5 mm (0.2 in) and preferably from about 0.8 mm (0.031 in) to about 3 mm (0.12 in). For a non-spherical inner core, effective diameter is defined as the diameter the shaped article would have if it were molded into a sphere. Once the inner core is prepared, it is calcined at a temperature of from about 400° C. (752° F.) to about 1800° C. (3272° F). When the inner core comprises cordierite, it is calcined at a temperature of from about 1000° C. (1832° F) to about 1800° C. (3272° F).

The inner core is coated with a layer of a refractory inorganic oxide which is different from the inorganic oxide which may be used as the inner core and will be referred to herein as the outer refractory inorganic oxide. This outer refractory inorganic oxide is one which has good porosity, has a surface area of to at least 20 $m^2/g$, and preferably at least 50 $m^2/g$, has an apparent bulk density of from about 0.2 g/ml to about 1.0 g/ml, and is chosen from the group consisting of gamma alumina, delta alumina, eta alumina, and theta alumina. Preferred outer refractory inorganic oxides are gamma alumina and eta alumina.

A preferred way of preparing a gamma alumina is by the well-known oil drop method which is described in U.S. Pat. No. 2,620,314 which is incorporated herein by reference. The oil drop method comprises forming an aluminum hydrosol by any of the techniques taught in the art and preferably by reacting aluminum metal with hydrochloric acid; combining the hydrosol with a suitable gelling agent, e.g., hexamethylenetetraamine; and dropping the resultant mixture into an oil bath maintained at elevated temperatures (about 93° C. (199° F.)). The droplets of the mixture remain in the oil bath until they set and form hydrogel spheres. The spheres are then continuously withdrawn from the oil bath and typically subjected to specific aging and drying treatments in oil and ammoniacal solutions to further improve their physical characteristics. The resulting aged and gelled spheres are then washed and dried at a relatively low temperature of about 80° C. (176° F.) to 260° C. (500° F.) and then calcined at a temperature of about 455° C. (851° F.) to 705° C. (1301° F.) for a period of about 1 to about 20 hours. This treatment effects conversion of the hydrogel to the corresponding crystalline gamma alumina.

The layer is applied by forming a slurry of the outer refractory oxide and then coating the inner core with the slurry by means well known in the art. Slurries of inorganic oxides can be prepared by means well known in the art which usually involve the use of a peptizing agent. For example, any of the transitional aluminas can be mixed with water and an acid such as nitric, hydrochloric, or sulfuric to give a slurry. Alternatively, an aluminum sol can be made by, for example, dissolving aluminum metal in hydrochloric acid and then mixing the aluminum sol with the alumina powder.

It is also preferred that the slurry contain an organic bonding agent which aids in the adhesion of the layer material to the inner core. Examples of this organic bonding agent include but are not limited to polyvinyl alcohol (PVA), hydroxy propyl cellulose, methyl cellulose, and carboxy methyl cellulose. The amount of organic bonding agent which is added to the slurry will vary considerably from about 0.1 wt-% to about 3 wt-% of the slurry. How strongly the outer layer is bonded to the inner core can be measured by the amount of layer material lost during an attrition test, i.e., attrition loss. Loss of the second refractory oxide by attrition is measured by agitating the catalyst, collecting the fines and calculating an attrition loss. It has been found that by using an organic bonding agent as described above, the attrition loss is less than about 10 wt-% of the outer layer. Finally, the thickness of the outer layer varies from about 40 microns (0.00158 in) to about 400 microns (0.0158 in), preferably from about 40 microns (0.00158 in) to about 300 microns (0.00181 in) and more preferably from about 45 microns (0.00177 in) to about 200 microns(0.00787 in). As used herein, the term "micron" means $10^{-6}$ meter.

Depending on the particle size of the outer refractory inorganic oxide, it may be necessary to mill the slurry in order to reduce the particle size and simultaneously give a narrower particle size distribution. This can be done by means known in the art such as ball milling for times of about 30 minutes to about 5 hours and preferably from about 1.5 to about 3 hours. It has been found that using a slurry with a narrow particle size distribution improves the bonding of the outer layer to the inner core.

The slurry may also contain an inorganic bonding agent selected from an alumina bonding agent, a silica bonding agent, or mixtures thereof. Examples of silica bonding agents include silica sol and silica gel, while examples of alumina bonding agents include alumina sol, boehmite, and aluminum nitrate. The inorganic bonding agents are converted to alumina or silica in the finished composition. The amount of inorganic bonding agent varies from about 2 to about 15 wt-% as the oxide, and based on the weight of the slurry.

Coating of the inner core with the slurry can be accomplished by means such as rolling, dipping, spraying, etc. One preferred technique involves using a fixed fluidized bed of inner core particles and spraying the slurry into the bed to coat the particles evenly. The thickness of the layer can vary considerably, but usually is from about 40 microns (0.00158 in) to about 400 microns (0.0158 in), preferably from about 40 microns (0.00158 in) to about 300 microns (0.0118 in) and most preferably from about 50 microns (0.001 97 in) to about 200 microns (0.00787 in). It should be pointed out that the optimum layer thickness depends on the use for the catalyst and the choice of the outer refractory oxide. Once the inner core is coated with the layer of outer refractory inorganic oxide, the resultant layered support is dried at a temperature of about 100° C. (212° F.) to about 320° C. (608° F.) for a time of about 1 to about 24 hours and then calcined at a temperature of about 400° C. (752° F.) to about 900° C. (1652° F.) for a time of about 0.5 to about 10 hours to effectively bond the outer layer to the inner core and provide a layered catalyst support. Of course, the drying and calcining steps can be combined into one step.

When the inner core is composed of a refractory inorganic oxide (inner refractory oxide), it is necessary that the outer refractory inorganic oxide be different from the inner refractory oxide. Additionally, it is required that the inner refractory inorganic oxide have a substantially lower adsorptive capacity for catalytic metal precursors relative to the outer refractory inorganic oxide.

Having obtained the layered catalyst support, catalytic metals can be dispersed on the layered support by means known in the art. Thus, a platinum group metal, a promoter metal, and a modifier metal can be dispersed on the outer layer. The platinum group metals include platinum, palladium, rhodium, iridium, ruthenium, and osmium. Promoter metals are selected from the group consisting of tin, germanium, rhenium, gallium, bismuth, lead, indium, cerium, zinc, and mixtures thereof, while modifier metals are selected from the group consisting of alkali metals, alkaline earth metals and mixtures thereof.

These catalytic metal components can be deposited on the layered support in any suitable manner known in the art. One method involves impregnating the layered support with a solution (preferably aqueous) of a decomposable compound of the metal or metals. By decomposable is meant that upon heating the metal compound is converted to the metal or metal oxide with the release of byproducts. Illustrative of the decomposable compounds of the platinum group metals are chloroplatinic acid, ammonium chloroplatinate, bromoplatinic acid, dinitrodiamino platinum, sodium tetranitroplatinate, rhodium trichloride, hexaamminerhodium chloride, rhodium carbonylchloride, sodium hexanitrorhodate, chloropalladic acid, palladium chloride, palladium nitrate, diamminepalladium hydroxide, tetraamminepalladium chloride, hexachloroiridate (IV) acid, hexachloroiridate (III) acid, ammonium hexachloroiridate (III), ammonium aquohexachloroiridate (IV), ruthenium tetrachloride, hexachlororuthenate, hexa-amminerutheniumchloride, osmium trichloride, and ammonium osmium chloride. Illustrative of the decomposable promoter metal compounds are the halide salts of the promoter metals. A preferred promoter is tin and preferred decomposable compounds are stannous chloride or stannic chloride.

The alkali. and alkaline earth metals which can be used as modifier metals in the practice of this invention include lithium, sodium, potassium, cesium, rubidium, beryllium, magnesium, calcium, strontium, and barium. Preferred modifier metals are lithium, potassium, sodium, and cesium with lithium and potassium being especially preferred. Illustrative of the decomposable compounds of the alkali and alkaline earth metals are the halide, nitrate, carbonate or hydroxide compounds, e.g., potassium hydroxide, lithium nitrate.

All three types of metals can be impregnated using one common solution or they can be sequentially impregnated in any order, but not necessarily with equivalent results. A preferred impregnation procedure involves the use of a steamjacketed rotary dryer. The support is immersed in the impregnating solution containing the desired metal compound contained in the dryer and the support is tumbled therein by the rotating motion of the dryer. Evaporation of the solution in contact with the tumbling support is expedited by applying steam to the dryer jacket. The resultant composite is allowed to dry under ambient temperature conditions, or dried at a temperature of about 80° C. (176° F.) to about 110° C. (230° F.), followed by calcination at a temperature of about 200° C. (392° F.) to about 700° C. (1292° F.) for a time of about 1 to about 4 hours, thereby converting the metal compound to the metal or metal oxide. It should be pointed out that for the platinum group metal compound, it is preferred to carry out the calcination at a temperature of about 400° C. (752° F.) to about 700° C. (1292° F.).

In one method of preparation, the promoter metal is first deposited onto the layered support and calcined as described above and then the modifier metal and platinum group metal are simultaneously dispersed onto the layered support by using an aqueous solution which contains a compound of the modifier metal and a compound of the platinum group metal. The support is impregnated with the solution as described above and then calcined at a temperature of about 400° C. (752° F.) to about 700° C. (1292° F.) for a time of about 1 to about 4 hours.

An alternative method of preparation involves adding one or more of the metal components to the outer refractory oxide prior to applying it as a layer onto the inner core. For example, a decomposable salt of the promoter metal, e.g., tin (IV) chloride, can be added to a slurry composed of gamma alumina and aluminum sol. Further, either the modifier metal or the platinum group metal or both can be added to the slurry. Thus, in one method, all three catalytic metals are deposited onto the outer refractory oxide prior to depositing the second refractory oxide as a layer onto the inner core. Again, the three types of catalytic metals can be deposited onto the outer refractory oxide powder in any order although not necessarily with equivalent results.

Another preferred method of preparation involves first impregnating the promoter metal onto the outer refractory inorganic oxide and calcining as described above. Next, a slurry is prepared (as described above) using the outer refractory inorganic oxide containing the promoter metal and applied to the inner core by means described above. Finally, the modifier metal and platinum group metal are simultaneously impregnated onto the layered composition which contains the promoter metal and calcined as described above to give the desired layered catalyst.

One particular method of preparation involves first preparing the outer refractory inorganic oxide using the oil drop method (as described above), except that the promoter metal is incorporated into the resulting mixture of hydrosol and the gelling agent prior to its being dropped into the oil bath. Thus, in this method, the aged and gelled spheres recovered from the oil bath contain the promoter metal. After washing, drying, and calcining (as described above), a slurry is prepared (as described above) using crushed spheres containing the promoter metal, and the slurry is applied to the inner core by means described above. The modifier metal and the platinum group metal are simultaneously impregnated onto the layered composition which contains the promoter metal and calcined (as described above) to give the desired layered catalyst. Another particular method of preparation involves preparing a slurry using the outer refractory inorganic oxide and then adding the promoter metal to the slurry. The slurry is then applied to the inner core by means described above. Finally, the modifier metal and the platinum group metal are simultaneously impregnated onto the layered composition and calcined to give the desired layered catalyst (as described above).

It is believed that other layered catalyst compositions and other methods of preparing such catalysts may also be suitable for preparing dehydrogenation catalysts that are useful in this invention. See, for example, U.S. Pat. No. 4,077,912 (Dolhyj et al.), U.S. Pat. No. 4,255,253 (Herrington et al.), and PCT International Publication Number WO 98/14274 (Murrell, et al.). Despite the seeming irrelevance of these three publications to catalytic dehydrogenation, it is believed that the teachings in these publications provide insight on layered dehydrogenation catalyst compositions.

As a final step in the preparation of the layered catalyst composition, the catalyst composition is reduced under hydrogen or other reducing atmosphere in order to ensure that the platinum group metal component is in the metallic state (zero valent). Reduction is carried out at a temperature of generally from about 100° C. (212° F.) to about 650° C. (1202° F.), preferably from about 300° C. (572° F.) to about 550° C. (1022° F.), for a time of about 0.5 to about 10 hours in a reducing environment, preferably dry hydrogen. The state of the promoter and modifier metals can be metallic (zero valent), metal oxide, or metal oxychloride.

The layered catalyst composition can also contain a halogen component which can be fluorine, chlorine, bromine, iodine, or mixtures thereof with chlorine and bromine preferred. This halogen component is present in an amount of 0.03 to about 0.3 wt-% with respect to the weight of the entire catalyst composition. The halogen component can be applied by means well known in the art and can be done at any point during the preparation of the catalyst composition although not necessarily with equivalent results. It is preferred to add the halogen component after all the catalytic components have been added either before or after treatment with hydrogen.

Although in the preferred embodiments all three metals are uniformly distributed throughout the outer layer of outer refractory oxide and substantially present only in the outer layer, it is also within the bounds of this invention that the modifier metal can be present both in the outer layer and the inner core. This is owing to the fact that the modifier metal can migrate to the inner core, when the core is other than a metallic core.

Although the concentration of each metal component can vary substantially, it is desirable that the platinum group metal be present in a concentration of about 0.01 to about 5 weight percent on an elemental basis of the entire weight of the catalyst and preferably from about 0.05 to about 1.0 wt-%. The promoter metal is present in an amount from about 0.05 to about 5 wt-% of the entire catalyst while the modifier metal is present in an amount from about 0.1 to about 5 wt-% and preferably from about 2 to about 4 wt-% of the entire catalyst. Finally, the atomic ratio of the platinum group metal to modifier metal varies from about 0.05 to about 5. In particular when the modifier metal is tin, the atomic ratio is from about 0.1:1 to about 5:1 and preferably from about 0.5:1 to about 3:1. When the modifier metal is germanium the ratio is from about 0.25:1 to about 5:1 and when the promoter metal is rhenium, the ratio is from about 0.05:1 to about 2.75:1.

The dehydrogenation conditions are selected to minimize cracking and polyolefin by-products. It is expected that typical dehydrogenation conditions will not result in any appreciable isomerization of the hydrocarbons in the dehydrogenation reactor. When contacting the catalyst, the hydrocarbon may be in the liquid phase or in a mixed vapor-liquid phase, but preferably it is in the vapor phase. Dehydrogenation conditions include a temperature of generally from about 400° C. (752° F.) to about 900° C. (1652° F.) and preferably from about 400° C. (752° F.) to about 525° C. (977° F.), a pressure of generally from about 1 kpa(g) (0.15 psi(g)) to about 1013 kPa(g) (147 psi(g)), and a LHSV of from about 0.1 to about 100 $hr^{-1}$. As used herein, the abbreviation "LHSV" means liquid hourly space velocity, which is defined as the volumetric flow rate of liquid per hour divided by the catalyst volume, where the liquid volume and the catalyst volume are in the same volumetric units. Generally for normal paraffins, the lower the molecular weight the higher the temperature required for comparable conversion. The pressure in the dehydrogenation zone is maintained as low as practicable, usually less than 345 kpa(g) (50 psi(g)), consistent with equipment limitations, to maximize chemical equilibrium advantages.

The isomerized product stream may be admixed with a diluent material before, while, or after being flowed to the dehydrogenation zone. The diluent material may be hydrogen, steam, methane, ethane, carbon dioxide, nitrogen, argon, and the like, or a mixture thereof. Hydrogen is the preferred diluent. Ordinarily, when hydrogen is utilized as the diluent it is utilized in amounts sufficient to ensure a hydrogen to hydrocarbon mole ratio of about 0.1:1 to about 40:1, with best results being obtained when the mole ratio range is about 1:1 to about 10:1. The diluent hydrogen stream passed to the dehydrogenation zone will typically be recycled hydrogen separated from the effluent from the dehydrogenation zone in the hydrogen separation zone.

Water or a material which decomposes at dehydrogenation conditions to form water such as an alcohol, aldehyde, ether, or ketone, for example, may be added to the dehydrogenation zone, either continuously or intermittently, in an amount to provide, calculated on the basis of equivalent water, about 1 to about 20,000 weight ppm of the hydrocarbon feed stream. About 1 to about 10,000 weight ppm of water addition gives best results when dehydrogenating paraffins having from 2 to 30 or more carbon atoms.

The monoolefin-containing dehydrogenated product stream from the paraffin dehydrogenation process is typically a mixture of unreacted paraffins, linear (unbranched) olefins, and branched monoolefins including lightly branched monoolefins. Typically, from about 25 to about 75 vol-% of the olefins in the monoolefin-containing stream from the paraffin dehydrogenation process are linear (unbranched) olefins.

The dehydrogenated product stream may comprise a highly branched monoolefin or a linear (unbranched) olefin, but, especially for the production of MAB, the monoolefin is preferably a lightly branched monoolefin. A lightly branched monoolefin, as used herein, refers to a monoolefin having a total number of carbon atoms of from about 8 to about 28, of which three or four of the carbon atoms are primary carbon atoms and none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms. Preferably, the lightly branched monoolefin has a total number of from 8 to 15 carbon atoms, and more preferably from 10 to 15 carbon atoms.

The lightly branched monoolefin generally comprises an aliphatic alkene having the general formula of $(p_i\text{-alkyl}_i)_i$-q-alkene. The lightly branched monoolefin consists of an aliphatic alkenyl chain, which is referred to by "alkene", in the $(p_i\text{-alkyl}_i)_i$-q-alkene formula, and is the longest straight chain containing the carbon-carbon double bond of the lightly branched monoolefin. The lightly branched monoolefin also consists of one or more alkyl group branches, each of which is attached to the aliphatic alkenyl chain and is designated by a corresponding "$(p_i\text{-alkyl}_i)_i$" in the $(p_i\text{-alkyl}_i)_i$-q-alkene formula. If it is possible to select two or more chains of equal lengths as the aliphatic alkenyl chain, the choice goes to the chain carrying the greatest number of alkyl group branches. The subscript counter "i" thus has a value of from 1 to the number of alkyl group branches, and for each value of i, the corresponding alkyl group branch is attached to carbon number $p_i$ of the aliphatic alkenyl chain. The double bond is between carbon number q and carbon number (q+1) of the aliphatic alkenyl chain. The aliphatic alkenyl chain is numbered from one end to the other, the direction being chosen so as to give the lowest number possible to the carbon atoms bearing the double bond.

The lightly branched monoolefin may be an alpha monoolefin or a vinylidene monoolefin, but is preferably an internal monoolefin. As used herein, the term "alpha olefins" refers to olefins having the chemical formula, R—CH=$CH_2$. The term "internal olefins," as used herein, includes di-substituted internal olefins having the chemical formula R-CH=CH-R; tri-substituted internal olefins having the chemical formula R-C(R)=CH-R; and tetra-substituted olefins having the chemical formula R-C(R)=C(R)-R. The di-substituted internal olefins include beta internal olefins having the chemical formula R-CH=CH-$CH_3$. As used herein, the term "vinylidene olefins" refers to olefins having the chemical formula R-C(R)=$CH_2$. In each of the preceding chemical formulas in this paragraph, R is an alkyl group that may be identical to or different from other alkyl group(s), if any, in each formula. Insofar as permitted by the definition of the term "internal olefin", when the lightly branched monoolefin is an internal monoolefin, any two carbon atoms of the aliphatic alkenyl chain may bear the double bond. Suitable lightly branched monoolefins include octenes, nonenes, decenes, undecenes, dodecenes, tridecenes, tetradecenes, pentadecenes, hexadecenes, heptadecenes, octadecenes, nonadecenes, eicosenes, heneicosenes, docosenes, tricosenes, tetracosenes, pentacosenes, hexacosenes, heptacosenes, and octacosenes.

For lightly branched monoolefins other than vinylidene olefins, the alkyl group branch or branches of the lightly branched monoolefin are generally selected from methyl, ethyl, and propyl groups, with shorter and normal branches being preferred. By contrast, for lightly branched monoolefins that are vinylidene olefins, the alkyl group branch attached to carbon number 2 of the aliphatic alkenyl chain may be selected not only from methyl, ethyl, and propyl groups but also from alkyl groups up to and including tetradecyl ($C_{14}$) groups, while any other alkyl group branch (es) of the vinylidene olefin is (are) generally selected from methyl, ethyl, and propyl groups with shorter and normal branches being preferred. For all lightly branched monoolefins, preferably the lightly branched monoolefin has only one alkyl group branch, but two alkyl group branches are also possible. Lightly branched monoolefins having either two alkyl group branches or four primary carbon atoms comprise generally less than 40 mol-%, and preferably less than about 30 mol-%, of the total lightly branched monoolefins, with the remainder of the lightly branched monoolefins having one alkyl group branch. Lightly branched monoolefins having either one alkyl group branch or three primary carbon atoms comprise preferably more than 70 mol-% of the total lightly branched monoolefins. Lightly branched monoolefins having only one alkyl group branch and where the sole alkyl group branch is a methyl group are referred to herein as monomethyl-alkenes and are a preferred component of the dehydrogenated product stream. Except for the alkyl group branch attached to carbon number 1 of the aliphatic alkenyl chain in a vinylidene olefin, any alkyl group branch can be bonded to any carbon on the aliphatic alkenyl chain.

Although vinylidene monoolefins may be present in the dehydrogenated product stream, they are normally a minor component and have a concentration of usually less than 0.5 mol-%, and more commonly less than 0.1 mol-%, of the olefins in the dehydrogenated product stream. Therefore, in the description that follows hereinafter, all references to the lightly branched monoolefins in general and to the dehydrogenated product stream in particular will assume that no vinylidene monoolefins are present.

The composition of a mixture of lightly branched monoolefins can be determined by analytical methods that are well-known to a person of ordinary skill in the art of gas chromatography and need not be described here in detail. A person of ordinary skill in the art can modify the apparatus and method in the previously mentioned article by Schulz et al. to equip the injector with a hydrogenator insert tube in order to hydrogenate the lightly branched monoolefins to lightly branched paraffins in the injector. The lightly branched paraffins are then separated and identified using essentially the apparatus and method described in the article by Schulz et al.

In addition to the lightly branched monoolefin, other acyclic compounds may be charged to the alkylation section via the dehydrogenated product stream. One of the advantages of this invention is that the stream containing the lightly branched monoolefins can be passed directly to the alkylation reaction section despite the fact that that stream also contains paraffins having the same number of carbon atoms as the lightly branched monoolefins. Thus, this invention avoids the need to separate the paraffins from the monoolefins prior to passing to the alkylation section. Other acyclic compounds include nonbranched (linear) olefins and monoolefins. Nonbranched (linear) olefins which may be charged have a total number of carbon atoms per paraffin molecule of generally from about 8 to about 28, preferably from 8 to 15, and more preferably from 10 to 14 carbon atoms. Two carbon atoms per nonbranched olefin molecule are primary carbon atoms and the remaining carbon atoms are secondary. carbon atoms. The nonbranched olefin may be an alpha monoolefin but is preferably an internal monoolefin. To the extent allowed by the definition of the term "internal olefin", when the nonbranched monoolefin is an internal monoolefin, any two carbon atoms of the aliphatic alkenyl chain may bear the double bond. When present in the dehydrogenated product stream with the lightly branched monoolefins, the linear olefin content may be as high as, or no more than, about 75 mol-% of the total monoolefins in the dehydrogenated product stream, but is generally less than about 40 mol-% of the total monoolefins in the dehydrogenated product stream.

Because of the possible presence in the dehydrogenated product stream of linear monoolefins, in addition to the lightly branched monoolefins, the bulk dehydrogenated product stream may contain, on average, fewer than 3, or between 3 and 4, primary carbon atoms per monoolefin molecule in the dehydrogenated product stream. Depending on the relative proportions of linear and lightly branched monoolefins, the dehydrogenated product stream, or the sum of all the monoolefins that pass to the alkylation zone, may have from 2.25 to 4 primary carbon atoms per monoolefin molecule.

Linear and/or nonlinear paraffins which pass to the alkylation section, via the dehydrogenated product stream, have a total number of carbon atoms per paraffin molecule of generally from about 8 to about 28, preferably from 8 to 15, and more preferably from 10 to 14 carbon atoms. The nonlinear paraffins in the dehydrogenated product stream may include lightly branched paraffins and may also include paraffins having at least one quaternary carbon atom. Such linear and nonlinear paraffins are expected to act as a diluent in the alkylation step and not to materially interfere with the alkylation step. However, the presence of such diluents in the alkylation reactor generally results in higher volumetric flow rates of process streams, and, in order to accommodate these higher flow rates, larger equipment in the alkylation reaction circuit (i.e., larger alkylation reactor and more alkylation catalyst),. and larger product recovery facilities may be required.

Monoolefins that are more highly branched than the lightly branched monoolefins may also be present in the dehydrogenated product stream, but because on alkylation such highly branched monoolefins tend to form BAB, preferably their concentration in the dehydrogenated product stream is minimized. For example, the dehydrogenated product stream may contain monoolefin molecules consisting of at least one quaternary carbon atom, which tend on alkylation to form phenyl-alkanes that have in the aliphatic alkyl portion a quaternary carbon atom that is not bonded by a carbon-carbon bond with a carbon atom of the aryl portion. Therefore, monoolefin molecules consisting of at least one quaternary carbon atom generally comprise less than 10 mol-%, preferably less than 5 mol-%, more preferably less than 2 mol-%, and most preferably less than 1 mol-% of the dehydrogenated product stream or of the sum of all the monoolefins that pass to the alkylation zone.

The lightly branched monoolefins are reacted with an aryl compound. In the general case, the lightly branched monoolefins could be reacted with other aryl compounds besides benzene, such as alkylated or otherwise substituted derivatives of benzene including toluene and ethylbenzene, but the product of such an alkylation may not be as suitable a detergent precursor as alkylated benzenes. But for detergent alkylation, the preferred aryl compound is benzene. Although the stoichiometry of the alkylation reaction requires only 1 molar proportion of aryl compound per mole of total monoolefins, the use of a 1:1 mole proportion results in excessive olefin polymerization and polyalkylation. That is, the reaction product under such conditions would consist not only of the desired monoalkylbenzenes, but also of large amounts of the dialkylbenzenes, trialkylbenzenes, possibly higher polyalkylated benzenes, olefin dimers, trimers, etc., and unreacted benzene. On the other hand, it is desired to have the aryl compound:monoolefin molar ratio as close to 1:1 as possible to maximize utilization of the aryl compound and to minimize the recycle of unreacted aryl compound. The actual molar proportion of aryl compound to total monoolefin will therefore have an important effect on both conversion and, perhaps more importantly, selectivity of the alkylation reaction. In order to carry out alkylation with the conversion and selectivity required using the catalysts of this invention's process, the total aryl compound: monoolefin molar ratio may be generally from about 2.5:1 up to about 50:1 and normally from about 8:1 to about 35:1.

The aryl compound and the lightly branched monoolefin are reacted under alkylation conditions in the presence of a solid alkylation catalyst. These alkylation conditions include a temperature in the range between about 176° F. (80° C.) and about 392° F. (200° C.), most usually at a temperature not exceeding 347° F. (175° C.). Since the alkylation is conducted in at least partial liquid phase, and preferably in either an all-liquid phase or at supercritical conditions, pressures for this embodiment must be sufficient to maintain reactants in the liquid phase. The requisite pressure necessarily depends upon the olefin, the aryl compound, and temperature, but normally is in the range of 200–1000 psi(g) (1379–6895 kPa(g)), and most usually 300–500 psi(g) (2069–3448 kPa(g)).

While the alkylation conditions are sufficient to alkylate the aryl compound with the lightly branched monoolefin, it is believed that under alkylation conditions only minimal skeletal isomerization of the lightly branched monoolefin occurs. As used herein, skeletal isomerization of an olefin under alkylation conditions means isomerization that occurs during alkylation and which changes the number of carbon atoms in the aliphatic alkenyl chain of the olefin, in the aliphatic alkyl chain of the phenyl-alkane product, or in any reaction intermediate that is formed or derived from the lightly branched monoolefin prior to the withdrawal of the phenyl-alkane product from the alkylation conditions. By minimal skeletal isomerization it is meant that generally less than 15 mol-%, and preferably less than 10 mol-%, of the olefin, the aliphatic alkyl chain, and any reaction intermediate undergoes skeletal isomerization. It is further believed that under alkylation conditions minimal skeletal isomerization occurs for any other olefins in the olefinic feedstock. Thus, alkylation preferably occurs in the substantial absence of skeletal isomerization of the lightly branched monoolefin, and the extent of light branching of the lightly branched monoolefin is identical to the extent of light branching in the aliphatic alkyl chain in the phenyl-alkane product molecule. Accordingly, the number of primary carbon atoms in the lightly branched monoolefin is preferably the same as the number of primary carbon atoms per phenyl-alkane molecule. Insofar as an additional methyl group branch does form on the aliphatic alkyl chain of the phenyl-alkane product, the number of primary carbon atoms in the phenyl-alkane product may be slightly higher the number of primary carbon atoms in the lightly branched monoolefin. Finally, although the formation of 1-phenyl-alkane product is not significant at alkylation conditions, insofar as a 1-phenyl-alkane molecule is formed by alkylating an aryl compound with a lightly branched monoolefin having a primary carbon atom on each end of the aliphatic alkenyl chain, the number of primary carbon atoms in the phenyl-alkane product will be slightly less than the number of primary carbon atoms in the lightly branched monoolefin.

The alkylation of the aryl compound with the lightly branched monoolefins produces $(m_i\text{-alkyl}_i)_i$-n-phenyl-alkanes, where the aliphatic alkyl group has two, three, or four primary carbon atoms per phenyl-alkane molecule. Preferably, the aliphatic alkyl group has three primary carbon atoms per phenyl-alkane molecule, and more preferably one of the three primary carbon atoms is in a methyl group at one end of the aliphatic alkyl chain, the second primary carbon atom is in a methyl group at the other end of the chain, and the third primary carbon atom is in a single methyl group branch attached to the chain. However, it is not necessary that all of the $(m_i\text{-alkyl}_i)$i-n-phenyl-alkanes produced by the present invention have the same number of primary carbon atoms per phenyl-alkane molecule. Generally from about 0 mol-% to about 75 mol-%, and preferably from about 0 mol-% to about 40 mol-%, of the $(m_i\text{-alkyl}_i)$$_i$-n-phenyl-alkanes produced may have 2 primary carbon atoms per phenyl-alkane molecule. Generally, as many as possible, and typically from about 25 mol-% to about 100 mol-%, of the $(m_i\text{-alkyl}_i)$i-n-phenyl-alkanes produced may have 3 primary carbon atoms per phenyl-alkane molecule. Generally from about 0 mol-% to about 40 mol-% of the $(m_i\text{-alkyl}_i)_i$-n-phenyl-alkanes produced may have 4 primary carbon atoms. Thus, (m-methyl)-n-phenyl-alkanes having only one methyl group branch are preferred and are referred to herein as monomethyl-phenyl-alkanes. It is expected that the number of primary, secondary, and tertiary carbon atoms per product arylalkane molecule can be determined by high resolution multipulse nuclear magnetic resonance (NMR) spectrum editing and distortionless enhancement by polarization transfer (DEPT), which is described in the brochure entitled "High Resolution Multipulse NMR Spectrum Editing and DEPT," which is distributed by Bruker Instruments, Inc., Manning Park, Billerica, Mass. USA, and which is incorporated herein by reference.

The alkylation of the aryl compound with the lightly branched monoolefins has a selectivity of 2-phenyl-alkanes of generally from about 40 to about 100 and preferably from about 60 to about 100, and an internal quaternary phenyl-alkane selectivity of generally less than 10 and preferably less than 5. Quaternary phenyl-alkanes can form by alkylating the aryl compound with a lightly branched monoolefin having at least one tertiary carbon atom. A tertiary carbon atom is a carbon atom which, while also possibly bonded to other atoms besides carbon, is bonded to only three carbon atoms. If, on alkylation, a tertiary carbon atom of the monoolefin forms a carbon-carbon bond with one of the carbon atoms of the aryl compound, that tertiary carbon atom becomes a quaternary carbon atom of the aliphatic alkyl chain. Depending on the location of the quaternary carbon atom with respect to the ends of the aliphatic alkyl chain, the resulting quaternary phenyl-alkane may be either an internal or an end quat.

Alkylation of the aryl compound by the lightly branched monoolefins may be conducted either as a batch method or in a continuous manner, although the latter is greatly preferred and therefore will be described in some detail. The composites of this invention used as catalyst may be used as a packed bed or a fluidized bed. The olefinic feedstock to the reaction zone may be passed either upflow or downflow, or even horizontally as in a radial bed reactor. The admixture of benzene and the olefinic feedstock containing the lightly branched monoolefins is introduced at a total aryl compound:monoolefin molar ratio of between 2.5:1 and 50:1, although usually the molar ratio is in the range between about 8:1 and 35:1. In one desirable variant, olefin may be fed into several discrete points within the reaction zone, and at each zone the aryl compound:monoolefin molar ratio may be greater than 50:1. However, the total benzene:olefin ratio used in the foregoing variant of this invention still will be within the stated range. The total feed mixture, that is, aryl compound plus olefinic feedstock containing lightly branched monoolefins, is passed through the packed bed at a liquid hourly space velocity (LHSV) between about 0.3 and about 6 hr$^{-1}$ depending upon alkylation temperature, how long the catalyst has been used, and so on. Lower values of LHSV within this range are preferred. The temperature in the reaction zone will be maintained at between about 80° C. and about 200° C. (176 to 392° F.), and pressures generally will vary between about 200 and about 1000 psi(g) (1379 to 6895 kPa(g)) to ensure a liquid phase or supercritical conditions. After passage of the aryl compound and the olefinic feedstock through the reaction zone, the effluent is collected and separated into unreacted aryl compound, which is recycled to the feed end of the reaction zone, paraffin, which is recycled to the dehydrogenation unit, and phenyl-alkanes. The phenyl-alkanes are usually further separated into the monoalkylbenzenes, used in subsequent sulfonation to prepare alkylbenzene sulfonates, and the oligomers plus polyalkylbenzenes. Since the reaction usually goes to at least about 98% conversion based on the monoolefin, little unreacted monoolefin is recycled with paraffin.

Any suitable alkylation catalyst may be used in the present invention, provided that the requirements for conversion, selectivity, and activity are met. Preferred alkylation catalysts comprise zeolites having a zeolite structure type selected from the group consisting of BEA, MOR, MTW, and NES. Such zeolites include mordenite, ZSM4, ZSM-12, ZSM-20, offretite, gmelinite, beta, NU-87, and gottardiite. These zeolite structure types, the term "zeolite structure type," and the term "isotypic framework structure" are used herein as they are defined and used in the *Atlas of Zeolite Structure Types*, by W. M. Meier, et al., published on behalf of the Structure Commission of the International Zeolite Association by Elsevier, Boston, Mass., USA, Fourth Revised Edition, 1996. Alkylations using NU-87 and NU-85, which is an intergrowth of zeolites EU-1 and NU-87, are described in U.S. Pat. Nos. 5,041,402 and 5,446,234, respectively. Gottardiite, which has an isotypic framework structure of the NES zeolite structure type, is described in the articles by A. Alberti et al., in Eur. J. Mineral., 8, 69–75 (1996), and by E. Galli et al., in Eur. J. Mineral., 8, 687–693 (1996). Most preferably, the alkylation catalyst comprises mordenite.

Useful zeolites for the alkylation catalyst in the present invention generally have at least 10 percent of the cationic sites thereof occupied by ions other than alkali or alkaline-earth metals. Such other ions include, but are not limited to hydrogen, ammonium, aluminum, rare earth, zinc, copper, and aluminum. Of this group, particular preference is accorded ammonium, hydrogen, rare earth, or combinations thereof. In a preferred embodiment, the zeolites are converted to the predominantly hydrogen form, generally by replacement of the alkali metal or other ion originally present with hydrogen ion precursors, e.g., ammonium ions, which upon calcination yield the hydrogen form. This exchange is conveniently carried out by contact of the zeolite with an ammonium salt solution, e.g., ammonium chloride, utilizing well known ion exchange techniques. In certain embodiments, the extent of replacement is such as to produce a zeolite material in which at least 50 percent of the cationic sites are occupied by hydrogen ions.

The zeolites may be subjected to various chemical treatments, including alumina extraction (dealumination) and combination with one or more metal components, such as the metals of Groups IIIB (IUPAC 3), IVB (IUPAC 4), VIB (IUPAC 6), VIIB (IUPAC 7), VIII (IUPAC 8-10), and IIB (IUPAC 12). It is also contemplated that the zeolites may, in some instances, desirably be subjected to thermal treatment, including steaming or calcination in air, hydrogen, or an inert gas, e.g. nitrogen or helium. A suitable steaming treatment comprises contacting the zeolite with an atmosphere containing from about 5 to about 100% steam at a temperature of from about 250° C. (482° F.) to 1000° C. (1832° F.). Steaming may last for a period of between about 0.25 and about 100 hours and may be conducted at pressures ranging from sub-atmospheric to several hundred atmospheres.

It may be useful to incorporate the zeolites that are useful in this invention in another material, e.g., a matrix material or binder that is resistant to the temperature and other conditions used in the process. Suitable matrix materials include synthetic substances, naturally occurring substances, and inorganic materials such as clay, silica, and/or metal oxides. Matrix materials can be in the form of gels including mixtures of silica and metal oxides. Gels including mixtures of silica and metal oxides may be either naturally occurring or in the form of gels or gelatinous precipitates. Naturally occurring clays. which can be composited with the zeolite used in this invention include those of the montmorillonite and kaolin families, which families include the sub-bentonites and the kaolins commonly known as Dixie, McNamee-Georgia, and Florida clays or others in which the main mineral constituent is halloysite, kaolinite, dickite, nacrite, or anauxite. Such clays can be used as a matrix material in their raw states as originally mined, or can be subjected to calcination, acid treatment or chemical modification prior to their use as matrix materials. In addition to the foregoing materials, the zeolite used in this invention may be compounded with a porous matrix material, such as alumina, silica-alumina, silica-magnesia, silica-zirconia, silica-thoria, silica-beryllia, silica-titania, and aluminum phosphate as well as ternary combinations, such as silica-alumina-thoria, silica-alumina-zirconia, silica-alumina-magnesia, and silica-magnesia-zirconia. The matrix material may be in the form of a cogel. The relative proportions of and matrix material may vary widely, with the zeolite content ranging generally from between about 1 and about 99% by weight, usually in the range of about 5 to about 80% by weight, and preferably in the range of about 30 to about 80% by weight, of the combined weight of zeolite and matrix material.

The zeolites that are useful in the alkylation catalyst generally have a framework silica:alumina molar ratio of from about 5:1 to about 100:1. When the zeolite of the alkylation catalyst is mordenite, the mordenite has a framework silica:alumina molar ratio generally of from about 12:1 to about 90:1, and preferably of from about 12:1 to about 25:1. As used herein, the term "framework silica:alumina molar ratio" means the molar ratio of silica per alumina, that is the molar ratio of $SiO_2$ per $Al_2O_3$, in the zeolite framework.

When zeolites have been prepared in the presence of organic cations they may not be sufficiently catalytically active for alkylation. Without being bound to any particular theory, it is believed that the insufficient catalytic activity is the result of the organic cations from the forming solution occupying the intracrystalline free space. Such catalysts may be activated, for example, by heating in an inert atmosphere at 540° C. (1004° F.) for one hour, ion exchanging with ammonium salts, and calcining at 540° C. (1004° F.) in air. The presence of organic cations in the forming solution may be essential to forming particular zeolites. Some natural zeolites may sometimes be converted to zeolites of the desired type by various activation procedures and other treatments such as ion exchange, steaming, alumina extraction, and calcination. When synthesized in the alkali metal form, the zeolite is conveniently converted to the hydrogen form, generally by intermediate formation of the ammonium form as a result of ammonium ion exchange and calcination of the ammonium form to yield the hydrogen form. Although the hydrogen form of the zeolite catalyzes the reaction successfully, the zeolite may also be partly in the alkali metal form.

The selective alkylation zone produces a selective alkylation zone effluent that enters separation facilities for the recovery of products and recyclable feed compounds. The selective alkylation zone effluent stream passes into a benzene column which produces an overhead stream containing benzene and a bottoms stream containing the alkylate product. This bottoms stream passes into a paraffin column which produces an overhead liquid stream containing unreacted paraffins and a bottoms stream containing the product alkylate and any higher molecular weight side product hydrocarbons formed in the selective alkylation zone. This paraffin column bottoms stream may pass to a rerun column which produces an overhead alkylate product stream containing the detergent alkylate and a rerun column bottoms stream containing polymerized olefins and polyalkylated benzenes (heavy alkylate). Alternatively, if the heavy alkylate content of the paraffin column bottoms stream is sufficiently low, a rerun column is not necessary and the paraffin column bottoms stream may be recovered as the net detergent alkylate stream from the process.

In accord with this invention, at least a portion of the overhead liquid stream of the paraffin column is recycled to the isomerization zone, the dehydrogenation zone, or both zones. Preferably, the portion of the overhead liquid stream of the paraffin column that is recycled to the isomerization zone or the dehydrogenation zone is an aliquot portion of the overhead liquid stream. An aliquot portion of the overhead liquid stream is a fraction of the overhead liquid stream that has essentially the same composition as the overhead liquid stream. The paraffin column overhead stream comprises paraffins having a total number of carbon atoms per paraffin molecule of generally from about 8 to about 28, preferably from 8 to 15, and more preferably from 10 to 15 carbon atoms. Preferably, at least a portion of the paraffin column overhead liquid stream is recycled to only the dehydrogenation zone. Generally, from about 50 to about 100 wt-% of the overhead liquid stream of the paraffin column is recycled to the isomerization zone and/or the dehydrogenation zone, and preferably all of the overhead liquid stream of the paraffin column is recycled to only the dehydrogenation zone.

Even though recycling the paraffin column overhead liquid stream to only the dehydrogenation zone is the preferred embodiment of this invention, it is useful to briefly describe the embodiment of this invention in which some of the paraffin column overhead liquid stream recycles to the isomerization zone. Regardless of whether recycling is to the isomerization zone or the dehydrogenation zone, the overhead stream of the paraffin column may contain both nonbranched (linear) paraffins and lightly branched paraffins, even if only nonbranched paraffins are charged to the process. This is because the skeletal isomerization zone typically converts from about 60 wt-% to about 80 wt-% of the entering nonbranched paraffins to lightly branched paraffins, the dehydrogenation zone typically converts from about 10 wt-% to about 15 wt-% of the entering paraffins to olefins, and the fraction of olefins in the dehydrogenated product stream that are lightly branched olefins is approximately the same as the fraction of paraffins in the isomerized product stream that are lightly branched paraffins. Thus, since the conversion of olefins in the alkylation zone is generally greater than 90 wt-% of the entering olefins, and more typically greater than 98 wt-%, and since the conversion of paraffins in the alkylation zone is essentially nil, the alkylation zone effluent will contain lightly branched paraffins. To illustrate this in operation, it is helpful to consider the initial operation of the subject process where only linear paraffins are charged to the isomerization zone. If the isomerization zone operates at a conversion of, say, x wt-%, of the entering nonbranched paraffins to lightly branched paraffins, then lightly branched paraffins will begin to appear in the overhead stream of the paraffin column. As these lightly branched paraffins are recycled to the isomerization zone, the mixture of paraffins charged to the isomerization zone will gradually shift from a mixture of only nonbranched paraffins to a mixture of nonbranched and lightly branched paraffins. Accordingly, the isomerization zone may then be operated at conditions so that the nonlinear paraffin conversion is less than x wt-%. Over time, the degree of isomerization conversion can be further adjusted until a steady state is established at which the rate of conversion of nonbranched paraffins to lightly branched paraffins in moles per unit time in the isomerization zone is approximately equal to the net rate at which MAB arylalkanes are recovered from the process. However, in a preferred embodiment of this invention where the paraffin column overhead liquid stream recycles only to the dehydrogenation zone, it is not necessary to adjust the degree of isomerization in the manner described in the preceding paragraph, since then the lightly branched paraffins are not recycling to the isomerization zone.

The paraffin column overhead liquid stream may contain monoolefins since olefin conversion in alkylation is not 100%. However, the concentration of monoolefins in the paraffin column overhead liquid stream is generally less than 0.3 wt-%. Monoolefins in the paraffin column overhead liquid stream may be recycled to the isomerization zone and/or the dehydrogenation zone. The paraffin column overhead liquid stream may also contain paraffins having at least one quaternary carbon atom, but preferably the concentration of such paraffins is minimized.

Several variants of the subject process are possible. One variant includes the selective hydrogenation of diolefins that may be present in the dehydrogenated product stream, since diolefins may be formed during the catalytic dehydrogenation of paraffins. Selective diolefin hydrogenation converts the diolefins to monoolefins, which are the desired product of the dehydrogenation section, and produces a selective diolefin hydrogenation product stream. The selective diolefin hydrogenation product stream has a lower concentration of diolefins than the dehydrogenated product stream.

Another variant of the subject process includes selective removal of aromatic by-products that may be present in the dehydrogenated product stream. Aromatic by-products may be formed during the catalytic dehydrogenation of paraffins, and these by-products may cause a number of deleterious effects, such as deactivation of the catalyst in the alkylation section, decreasing the selectivity to the desired arylalkanes, and accumulation to unacceptable concentration in the process. Suitable aromatics removal zones include sorptive separation zones containing a sorbent such as a molecular sieve and in particular 13× zeolite (sodium zeolite X), and liquid-liquid extraction zones. Selective removal of these aromatic by-products may be accomplished in one or more locations of the subject process. The aromatic by-products may be selectively removed from, for example, the isomerized product stream, the dehydrogenated product steam, or the overhead liquid stream of the paraffin column that is recycled to the isomerization zone or the dehydrogenation zone. Where the subject process includes a selective diolefin hydrogenation zone the aromatic byproducts may be selectively removed from the selective diolefin hydrogenation product stream. The selective aromatics removal zone produces a stream that has a decreased concentration of aromatic by-products than that of the stream passed to the selective aromatics removal zone. Detailed information on selective removal of aromatic by-products from an alkylaromatic process for the production of linear alkylbenzenes is disclosed in U.S. Pat. No. 5,276,231, the teachings of which are incorporated herein by reference. It is believed that a person of ordinary skill in the art is capable of modifying the teachings of U.S. Pat. No. 5,276,231 with respect to aromatic by-products removal, including choice of sorbent, operating conditions, and location in the process, so as to successfully remove aromatic by-products from a process for the production of MAB.

Although the selective removal of these aromatic by-products is preferably accomplished on a continuous basis, selective removal may also be done intermittently or on a batch-wise basis. Intermittent or batch-wise removal would be most useful when the capacity of the removal zone to remove the aromatic by-products from the process exceeds the rate at which aromatic by-products accumulate in the process. If, in addition, some variation in the level or concentration of aromatic by-products within the process is acceptable or tolerable, then the aromatic by-products selective removal zone could be placed on-stream in one of the above mentioned locations for a specified period of time until the concentration or level of aromatic by-products in the process is decreased to a sufficient minimum concentration. Then the aromatic by-products selective removal zone could be taken off-stream or bypassed until the concentration increases to the tolerable maximum concentration, at which time the removal zone could be placed on-stream again.

In a preferred embodiment of the process aspect of this invention, this invention is a process for producing a preferred MAB composition comprising arylalkanes having one aryl group and one aliphatic alkyl group, wherein the arylalkanes have:

(i) an average weight of the aliphatic alkyl groups of the arylalkanes of between the weight of a $C_{10}$ aliphatic alkyl group and a $C_{13}$ aliphatic alkyl group;

(ii) a content of arylalkanes having the phenyl group attached to the 2-and/or 3-position of the aliphatic alkyl group of greater than 55 wt-% of the arylalkanes; and (iii) an average level of branching of the aliphatic alkyl groups of the arylalkanes of from 0.25 to 1.4 alkyl group branches per arylalkane molecule when the sum of the contents of 2-phenyl-alkanes and 3-phenyl-alkanes is more than 55 wt-% and less than or equal to 85 wt-% of the arylalkanes, or an average level of branching of the aliphatic alkyl groups of the arylalkanes of from 0.4 to 2.0 alkyl group branches per arylalkane molecule when the sum of the concentrations of 2-phenyl-alkanes and the 3-phenyl-alkanes is greater than 85 wt-% of the arylalkanes; and (iv) wherein the aliphatic alkyl groups of the arylalkanes comprise primarily linear aliphatic alkyl groups, mono-branched aliphatic alkyl groups, or di-branched aliphatic alkyl groups, and wherein the alkyl group branches if any on the aliphatic alkyl chain of the aliphatic alkyl groups comprise primarily small substituents, such as methyl group branches, ethyl group branches, or propyl group branches, and wherein the alkyl group branches if any attach to any position on the aliphatic alkyl chain of the aliphatic alkyl groups provided that arylalkanes having at least one quaternary carbon atom on the aliphatic alkyl group comprise less than 20% of the arylalkanes.

One process for producing this preferred MAB composition comprises isomerizing paraffins having an average weight between the weight of a $C_{10}$ paraffin and a $C_{13}$ paraffin to produce isomerized paraffins having an average level of branching of from 0.25 to 1.4, or of from 0.4 to 2.0, alkyl group branches per paraffin molecule. These isomerized paraffins primarily comprise linear paraffins, mono-branched paraffins, or di-branched paraffins, and the alkyl group branches if any on the aliphatic alkyl chain of the isomerized paraffins primarily comprise small substituents, such as methyl group branches, ethyl group branches, or propyl group branches. The alkyl group branches of the isomerized paraffins may be attached to any position on the aliphatic alkyl chain of the paraffin, subject to certain limitations that depend on the desired characteristics of the resultant arylalkanes. The isomerized paraffins are dehydrogenated to produce the corresponding isomerized mono-olefins, which alkylate an aryl compound to produce arylalkanes. The resultant arylalkanes have the characteristics that the arylalkanes having the phenyl group attached to the 2-and/or 3-position of the aliphatic alkyl group comprise greater than 55 wt-% of the arylalkanes, and the arylalkanes having at least one quaternary carbon atom on the aliphatic alkyl group comprise less than 20% of the arylalkanes.

Sulfonation of the arylalkanes produced by the processes of this invention can be accomplished by contacting the arylalkane compounds with any of the well-known sulfonation systems, including those described in *Detergent Manufacture Including Zeolite Builders and Other New Materials*, by Marshall Sittig, Noyes Data Corporation, Park Ridge, N.J., 1979, and in Volume 56 of "Surfactant Science" series, Marcel Dekker, Inc., New York, N.Y., 1996. Sulfonation of the arylalkane compounds produces a sulfonated product comprising arylalkane sulfonic acids. Common sulfonation systems employ sulfonating agents such as sulfuric acid, chlorosulfonic acid, oleum, and sulfur trioxide. Sulfonation using a mixture of sulfur trioxide and air is described in U.S. Pat. No. 3,427,342.

After sulfonation, the sulfonated product can be neutralized by contact with any suitable alkali, such as sodium, potassium, ammonium, magnesium, calcium, and substituted ammonium alkalis, and mixtures thereof. Neutralization of the arylalkane sulfonic acids produces a neutralized product comprising arylalkane sulfonates. Suitable neutralizing agents include sodium hydroxide, potassium hydroxide, ammonium hydroxide, sodium carbonate, sodium bicarbonate, potassium carbonate, magnesium hydroxide, magnesium carbonate, basic magnesium carbonate (magnesia alba), calcium hydroxide, and calcium carbonate, and mixtures thereof.

In other aspects of the present invention, this invention is the MAB compositions and the MABS compositions produced by the processes disclosed herein.

In yet another aspect of the present invention, this invention is the use of the MAB compositions produced by the processes disclosed herein as lubricants. These arylalkanes are believed to have properties of viscosity, temperature-dependence of viscosity, and density that make them advantageous for use as petroleum lubricants. The use of arylalkanes as lubricants is described, for example, in the article by E. R. Booser in *Kirk-Othmer Encyclopedia of Chemical Technology*, Fourth Edition, Volume 15, John Wiley and Sons, New York, N.Y., USA, 1995, pp. 463–517, to which reference is made for a description of such lubricants and their use.

In still another aspect, this invention is the use of the MABS compositions produced by the processes disclosed herein as lubricant additives. It is believed that arylalkane sulfonates, either in the form of normal salts or basic salts of arylalkane sulfonic acids, produced as disclosed herein, have the ability to reduce or prevent deposits in engines operating at high temperatures. As used herein, the term "normal salt" of an acid means a salt which contains the stoichiometric amount of metal required for the neutralization of the acidic group or groups present, and the term "basic salt" means a salt which contains more metal than is required for the neutralization reaction. The excess metal, in the form of basic salts is believed to be capable of neutralizing oil oxidation combustion products and "blow-by" fuel combustion products. Arylalkane sulfonates and their use as lubricant additives, in particular as detergents, is described, for example, in the above-mentioned Booser article; in *Lubricant Additives*, by C. V. Smalheer and R. K. Smith, The Lezius-Hiles Co., Cleveland, Ohio, USA, 1967, pp. 2–3; and in the article by R. W. Watson and T. F. McDonnell, Jr., entitled "Additives-The Right Stuff for Automotive Engine Oils,", in *Fuels and Lubricants Technology: An Overview* SP-603, Society of Automotive Engineers, Warrendale, Pennsylvania, USA, October 1984, pp. 17–28.

A complete operation of the process aspect of this invention can be more fully understood from a process flow for a preferred embodiment of this invention.

The drawing shows a preferred arrangement for an integrated isomerization-dehydrogenation-alkylation scheme of this invention.

The following description of the drawing is not meant to preclude other arrangements for the process flow of this invention and is not intended to limit this invention as set forth in the claims.

Referring now to the drawing, a paraffin feed comprising an admixture of $C_{10}$–$C_{13}$ normal paraffins is charged to a line 12. The normal paraffins in line 12 are admixed with a hydrogen-containing stream from line 22 and the admixture passes through line 16. A mixture of paraffins and hydrogen flowing through line 16 is first heated in the indirect heat exchanger 18 and is then passed through a line 24 into a fired heater 20. Alternatively, instead of admixing the hydrogen-containing stream in line 22 with the normal paraffins upstream of both exchanger 18 and heater 20 as shown in the drawing, the stream in line 22 may be admixed with the normal paraffins between the exchanger 18 and the heater 20 or between the heater 20 and the reactor 30. The resultant mixture of hydrogen and liquid paraffins passes through line 26 into an isomerization reactor 30. Inside the reactor 30, the paraffins are contacted in the presence of an isomerization catalyst at conditions which effect the conversion of a significant amount of the normal paraffins to lightly branched paraffins. There is thus produced an isomerization reactor effluent stream carried by line 28 which comprises a mixture of hydrogen, normal paraffins, and lightly branched paraffins. This isomerization reactor effluent stream is first cooled by indirect heat exchanger in the heat exchanger 18 and after passing through a line 32 is then further cooled in an indirect heat exchanger 34. This cooling is sufficient to condense substantially all of the $C_{10}$-plus hydrocarbons into a liquid phase stream and to separate the liquid phase stream from the remaining vapor, which is rich in hydrogen. This isomerization reactor effluent stream then passes through a line 36 and enters the vapor-liquid separation vessel 38, wherein it is divided into a hydrogen-rich vapor phase stream removed through line 40 and an isomerized product stream removed through line 50. The vapor phase stream is divided into a net purge stream to remove $C_1$–$C_7$ light hydrocarbons through a line 42 and a hydrogen stream that is recycled by line 44. The hydrogen stream in line 44 is combined with a hydrogen make-up stream that is charged to line 46. The combination of the hydrogen stream in line 44 and the make-up stream in line 46 produces the recycle stream in line 22.

The isomerized product stream removed from the bottom of the separation vessel 38 contains normal paraffins, lightly branched paraffins, and some dissolved hydrogen. The isomerized product stream, which is the liquid phase portion of the effluent of the separation vessel 38, is then passed through line 50 to combine with recycle paraffins in a line 48. The combined stream of paraffins flows through a line 54 and is admixed with recycled hydrogen from a line 82 to form a mixture of paraffins and hydrogen that flows through a line 56. The mixture of paraffins and hydrogen flowing through the line 56 is first heated in an indirect heat exchanger 58 and then passes through a line 62 to a fired heater 60. The two-phase mixture of hydrogen and liquid paraffins that is withdrawn from the fired heater 60 passes through a line 64 into a dehydrogenation reactor 70. Inside the dehydrogenation reactor 70, the paraffins contact a dehydrogenation catalyst at conditions which effect the conversion of a significant amount of the paraffins to the corresponding olefins. There is thus produced a dehydrogenation reactor effluent stream carried by line 66 which comprises a mixture of hydrogen, paraffins, monoolefins including. lightly branched monoolefins, diolefins, $C_9$-minus hydrocarbons, and aromatic hydrocarbons. This dehydrogenation reactor effluent stream is first cooled by indirect heat exchange in the heat exchanger 58, passes through a line 68, and is then further cooled in an indirect heat exchanger 72. This cooling is sufficient to condense substantially all of the $C_{10}$-plus hydrocarbons into a liquid phase stream and separate the liquid phase stream from the remaining hydrogen-rich vapor. This dehydrogenation reactor effluent stream flows through a line 74 and enters the vapor-liquid separation vessel 80. In the separation vessel 80, the dehydrogenation reactor effluent stream is divided into a hydrogen-rich vapor phase stream removed through a line 76 and a dehydrogenation product stream removed through a line 84. The vapor phase stream is divided into a net hydrogen product stream removed through a line 78 and the hydrogen-containing stream that is recycled by the line 82.

The dehydrogenated product stream removed from the bottom of the separation vessel 80 contains normal paraffins, lightly branched paraffins, normal monoolefins, lightly branched monoolefins, $C_9$-minus hydrocarbons, diolefins, aromatic by-products, and some dissolved hydrogen. The dehydrogenated product stream, which is the liquid phase effluent of the separator vessel 80, is then passed through a line 84 to a selective hydrogenation reactor 86. Inside the selective hydrogenation reactor 86, the dehydrogenated product stream is contacted in the presence of a selective hydrogenation catalyst at conditions which effect the conversion of a significant amount of the diolefins to the corresponding monoolefins. This conversion by hydrogenation can be effected using the dissolved hydrogen in the dehydrogenated product stream and/or additional make-up hydrogen (not shown) charged to the selective hydrogenation reactor. There is thus produced a selective hydrogenation reactor effluent stream carried by a line 88, which comprises a mixture of hydrogen, normal paraffins, lightly paraffins, normal monoolefins, lightly branched monoolefins, $C_9$-minus hydrocarbons, and aromatic by-product hydrocarbons. This selective hydrogenation reactor effluent is then passed through the line 88 to a stripping column 90. In this stripping column, the $C_9$-minus hydrocarbons produced in the dehydrogenation reactor as by-products and any remaining dissolved hydrogen are separated from the $C_{10}$-plus hydrocarbons and concentrated into a net overhead stream removed from the process through a line 94.

The remainder of the hydrocarbons entering the stripping column 90 are concentrated into a stripping effluent stream carried by a line 96. The stripping effluent stream is then passed into an aromatics removal zone 100. In this zone, the stripping effluent stream is contacted with an adsorbent under conditions which promote the removal of the aromatic by-products. The effluent from the aromatics removal zone 100 is transferred via a line 98. This stream comprises an admixture of the normal paraffins, lightly branched paraffins, normal monoolefins, and lightly branched monoolefins, and has a greatly reduced concentration of aromatic by-products compared to the stripping effluent stream. This admixture is combined with benzene from a line 112 and passed via a line 102 into an alkylation reactor 104. In the alkylation reactor, benzene and the monoolefins are contacted with an alkylation catalyst at alkylation-promoting conditions to produce arylalkanes.

The alkylation reactor effluent stream is carried by a line 106 and passes into a benzene fractionation column 110 by a line 106. This stream comprises an admixture of benzene, normal paraffins, lightly branched paraffins, arylalkanes comprising one aryl portion and one aliphatic alkyl portion having 1 or 2 primary carbon atoms, and arylalkanes comprising one aliphatic alkyl portion and one aryl portion where the aliphatic alkyl portion has 2, 3, or 4 primary carbon atoms and has no quaternary carbon atoms except for any quaternary carbon atom bonded to the aryl portion. In other words, this stream comprises an admixture of benzene, normal paraffins, lightly branched paraffins, LAB, and MAB. This stream is separated in benzene fractionation column 110 into a bottom stream and an overhead stream comprising benzene and possibly light gases. The overhead stream is carried by a line 107 and combines with make-up benzene charged to a line 109. The combined stream flows through a line 108 to a separator drum 120 from which noncondensed light gases, if any, are removed via a line 114 and condensed liquid is withdrawn by a line 116 to supply reflux to column 110 via a line 118 and benzene for recycle by a line 112. A line 122 carries the remainder of the alkylation effluent stream from column 110 to a paraffin column 124 from which a bottom stream containing the arylalkanes and heavy alkylate by-products is taken by a line 126. The contents of line 126 are separated in a rerun column 130 into a bottom stream 132 comprising heavy alkylate and an overhead alkylate product stream 128 containing the arylalkane compounds. The overhead stream from the paraffin column 124 is a recycle stream that contains a mixture of paraffins that are recycled to the dehydrogenation zone via the line 48. Although not shown in the drawing, some of the overhead stream from the paraffin column 124 may be passed to the isomerization zone rather than to the dehydrogenation zone.

As alternatives to the process flow shown in the drawing, the overhead stream in line 48 may be introduced into the dehydrogenation zone at other locations, such as into line 62, line 64, or reactor 70. In the case where the location is the dehydrogenation reactor 70, the overhead stream may be introduced at an intermediate point between the inlet of line 64 and the outlet of line 66, so that the overhead stream might contact only a portion of the catalyst in the dehydrogenation reactor 70. Another way of contacting the overhead stream with some but not all of the dehydrogenation catalyst is to divide the dehydrogenation reactor 70 into two or more catalyst-containing subreactors connected in a series flow arrangement by one or more lines, and to introduce the overhead stream into a line between subreactors. Whether an intermediate introduction point in the dehydrogenation reactor 70 is preferred depends on factors including the olefin content of the overhead stream and the dehydrogenation reaction conditions including conversion. Similarly, in the embodiment where the overhead stream in line 48 is introduced to the isomerization zone, the point of introduction may be upstream of the inlet of line 26 to the isomerization reactor 30 so that the overhead stream might contact all of the catalyst in the isomerization reactor 30. However, depending on the isomerization reaction conversion, the degree of branching of the overhead stream in line 48, and other factors, the point of introduction may be an intermediate point between the inlet of line 26 and the outlet of line 28, thereby resulting in the overhead stream contacting only some of the catalyst in the isomerization reactor 30. The isomerization reactor 30 may be divided into two or more smaller reactors in series, so that the overhead stream may be introduced to pass through some but not all of the isomerization reactors. By analyzing the composition of the isomerized product, dehydrogenated product, and alkylate product streams, a person of ordinary skill in the art is able to select the preferred point of introduction for recycling the overhead stream into the process.

Sulfonation of the arylalkane compounds in the overhead alkylate product stream 128 can be accomplished as hereinbefore described to produce arylalkane sulfonic acids, which can be neutralized as hereinbefore described.

The following examples are presented to illustrate this invention and are not intended as undue limitations in the generally broad scope of the invention as set forth in the claims.

EXAMPLES

Examples 1 and 2 illustrate the use of preferred isomerization catalysts for this invention. The following procedure was employed in both Examples 1 and 2. A 20 cc sample of isomerization catalyst was placed in a tubular reactor having an inside diameter of 1.27 cm (0.5 in). The isomerization catalyst was pre-reduced by contact with 1.0 SCFH (0.027 $Nm^3$/h) of hydrogen at 10 psi(g) (69 kPa(g)) while the catalyst temperature was held at 110° C. (230° F.) for 1 hour, increased from 110° C. (230° F.) to 400° C. (752° F.) over 3 hours, and then held at 400° C. (752° F.) for 2 hours. After this pre-reduction, the isomerization catalyst was cooled to about 150° C. (302° F.).

Next, the catalyst was tested for isomerization using a feed mixture of $C_{10}$–$C_{14}$ linear paraffins. The feed mixture ("feed",) was passed over the isomerization catalyst at a LHSV of 5 $hr^{-1}$, at a molar ratio of hydrogen per hydrocarbon of 1.5:1, and at a pressure of 500 psi(g) (3447 kPa(g)). The catalyst temperature was adjusted to achieve a desired conversion of the linear paraffins. The effluent of the tubular reactor was passed to a gas-liquid separator, and a liquid phase ("product",) was collected from the separator. The product was analyzed by gas chromatography as already described herein.

The individual components determined by gas chromatograph of the feed and the product were grouped into five classifications for purposes of Examples 1 and 2: light products having 9 or less carbon atoms ($C_9-$); linear paraffins having 10 to 14 carbon atoms ("linear",); monomethyl-branched paraffins having 10 to 14 carbon atoms in the product ("mono"); dimethyl-branched paraffins and ethyl-branched paraffins having 10 to 14 carbon atoms in the product ("di",); and heavy products having 15 or more carbon atoms ($C_{15}+$). Based on these five groupings, the following performance measures were computed:

i. Conversion:

Conversion=100×[1−(linears in product)/(linears in feed)].

ii. Monomethyl selectivity:

Monomethyl selectivity=100×[mono/(mono+di)].

iii. Lights yield:

Lights yield=100×[$C_9-(C_9-+$(linears in product)+mono+di+$C_{15}+$)].

iV. Heavies yield:

Heavies yield=100×[$C_{15}+/(C_9-+$(linears in product)+mono+di+$C_{15}+$)].

EXAMPLE 1

The catalyst for Example 1 was prepared by coextruding 0.39 wt-% Pt on a support comprising an extrudate of 60 wt-% SAPO-11 and 40 wt-% alumina. During isomerization, the conversion was 73.4 mol-%, the monomethyl selectivity was 55.5 mol-%, the lights yield was 7.9 mol-%, and the heavies yield was 0.01 mol-%.

EXAMPLE 2

The catalyst for Example 2 was prepared by impregnating 0.26 wt-% Pt with 50 wt-% MgAPSO-31 and 50 wt-% alumina. During isomerization, the conversion was 73.3 mol-%, the monomethyl selectivity was 69.6 mol-%, the lights yield was 13.5 mol-%, and the heavies yield was less than 0.01 mol-%.

Examples 1 and 2 show the good conversion and high selectivity to monomethyl paraffins that can be achieved with isomerization catalysts comprising SAPO-11 and MgAPSO-31.

Examples 3 through 7 illustrate the use of preferred dehydrogenation catalysts for this invention.

EXAMPLE 3

Example 3 illustrates a preferred dehydrogenation catalyst for use in this invention, and a method of preparing the catalyst. Alumina spheres were prepared by the well known oil drop method which is described in U.S. Pat. No. 2,620,314 which is incorporated by reference. This process involves forming an aluminum hydrosol by dissolving aluminum in hydrochloric acid. Hexamethylene tetraamine was added to the sol to gel the sol into spheres when dispersed as droplets into an oil bath maintained at about 93° C. (199° F.). The droplets remained in the oil bath until they set and formed hydrogel spheres. After the spheres were removed from the hot oil, they were pressure aged at 135° C. (275° F.) and washed with dilute ammonium hydroxide solution, dried at 110° C. (230° F.), and calcined at 650° C. (1202° F.) for about 2 hours to give gamma alumina spheres. The calcined alumina was crushed into a fine powder having a particle size of less than 200 microns (0.00787 in).

Next, a slurry was prepared by mixing 258 g of an aluminum sol (20 wt-% $Al_2O_3$) and 6.5 g of a 50% aqueous solution of tin chloride and 464 g of deionized water and agitated to uniformly distribute the tin component. To this mixture there were added 272 g of the above prepared alumina powder, and the slurry was ball milled for 2 hours thereby reducing the maximum particle size to less than 40 microns (0.00158 in). This slurry (1000 g) was sprayed onto 1 kg of alpha alumina cores having an average diameter of about 1.05 mm (0.0413 in) by using a granulating and coating apparatus for 17 minutes to give an outer layer of about 74 microns (0.00291 in). At the end of the process, 463 g of slurry were left which did not coat the cores. This layered spherical support was dried at 150° C. (302° F.) for 2 hours and then calcined at 615° C. (1139° F.) for 4 hours in order to convert the pseudoboehmite in the outer layer into gamma alumina and convert the tin chloride to tin oxide.

The calcined layered support (1150 g) was impregnated with lithium using a rotary impregnator by contacting the support with an aqueous solution (1:1 solution: support volume ratio) containing lithium nitrate and 2 wt-% nitric acid based on support weight. The impregnated catalyst was heated using the rotary impregnator until no solution remained, dried, and then calcined at 540° C. (1004° F.) for 2 hours.

The tin and lithium containing composite was now impregnated with platinum by contacting the above composite with an aqueous solution (1:1 solution: support volume ratio) containing chloroplatinic acid and 1.2 wt-% hydrochloric acid (based on support weight). The impregnated composite was heated using the rotary impregnator until no solution remained, dried, calcined at 540° C. (1004° F.) for 2½ hours, and reduced in hydrogen at 500° C. (932° F.) for 2 hours. Elemental analysis showed that this catalyst contained 0.093 wt-% platinum, 0.063 wt-% tin and 0.23 wt-% lithium with respect to the entire catalyst. The distribution of the platinum was determined by Electron Probe Micro Analysis (EPMA) using a Scanning Electron Microscope which showed that the platinum was evenly distributed throughout the outer layer only.

EXAMPLE 4

The catalyst of Example 3 was tested for dehydrogenation activity. In a 1.27 cm (0.5 in) reactor, 10 cc of catalyst was placed and a hydrocarbon feed composed of 8.8 wt-% n-$C_{10}$, 40.0 wt-% n-$C_{11}$, 38.6 wt-% n-$C_{12}$, 10.8 wt-% n-$C_{13}$, 0.8 wt-% n-$C_{14}$ and 1 vol-% non-normals was flowed over the catalyst under a pressure of 138 kPa(g) (20 psi(g)), a hydrogen hydrocarbon molar ratio of 6:1, and a LHSV of 20 $hr^{-1}$. Water at a concentration of 2000 ppm based on hydrocarbon weight was injected. The total normal olefin concentration in the product (%TNO) was maintained at 15 wt-% by adjusting reactor temperature.

The results of the testing are as follows. Selectivity for TNO at 120 hours on stream, which is calculated by dividing %TNO by total conversion, is 94.6 wt-%. Non-TNO selectivity, which is calculated as 100%—%TNO, is 5.4 wt-%.

The results show that the layered catalyst useful in this invention has both low deactivation rate and high selectivity to normal olefins. Because the hydrocarbon feed in this example comprised mostly normal paraffins, the high selectivity for TNO indicates that relatively little skeletal isomerization of the hydrocarbon feed occurred during dehydrogenation.

EXAMPLE 5

The procedure set forth in Example 3 was used to prepare a catalyst with the modification that polyvinyl alcohol (PVA) at a concentration of 2 wt-% of the gamma alumina was added to the slurry. This catalyst was identified as catalyst A.

EXAMPLE 6

The procedure in Example 3 was used to prepare a catalyst with a layer thickness of 90 microns (0.00354 in). This catalyst was identified as catalyst B.

EXAMPLE 7

Catalysts A and B were tested for loss of layer material by attrition using the following test.

A sample of the catalyst was placed in a vial which in turn was placed in a blender mill along with another vial containing the same amount of catalyst sample. The vials were milled for ten (10) minutes. The vials were removed and then sieved to separate the powder from the spheres. The powder was weighed and an attrition loss (wt-%) was calculated.

The results of the attrition test are summarized in Table 1.

TABLE 1

Effect of Organic Binding Agent on Attrition

| Catalyst | Weight Percent Loss | |
|---|---|---|
| | Based on Total Amount | Based On Layer |
| A (PVA) | 1.0 | 4.3 |
| B (No Additive) | 3.7 | 17.9 |

The data in Table 1 show that using an organic binding agent greatly improves the attrition loss of a layered catalyst.

Examples 8 and 9 illustrate the use of a preferred alkylation catalyst for this invention.

EXAMPLE 8

Example 8 illustrates an alkylation catalyst for use in this invention that was formulated by a method consistent with that of an alkylation catalyst. The starting material was the hydrogen form of a mordenite having a $SiO_2/Al_2O_3$ of 18, hereinafter referred to as the starting mordenite. 90 parts by weight of the starting mordenite were mixed with 10 parts by weight of alumina powder. An acidified peptization solution was added to the mixture. The admixture was then extruded by means known in the art. After the extrusion process, the extrudate was dried and calcined. Following the drying and calcining steps, the extrudate was washed with an aqueous solution comprising 3 wt-% HCl for 2 hours at 66° C. (151° F.) at a solution to extrudate volume ratio of about 6:1. After the wash step, the extrudate was rinsed for 1 hour with water at a solution to extrudate volume ratio of about 5:1, and then dried.

EXAMPLE 9

Example 9 illustrates the use of the alkylation catalyst in Example 8.

An olefinic feedstock comprising a blend of monomethyl $C_{12}$ olefins and having the composition shown in Table 2 was used.

TABLE 2

Composition of Olefinic Feedstock

| Olefin Component | Content (wt-%) |
|---|---|
| Lights[1] | 0.64 |
| Linear olefins[2] | 30.11 |
| 6-methyl undecene | 7.66 |
| 5-methyl undecene | 15.33 |
| 4-methyl undecene | 11.82 |
| 3-methyl undecene | 12.95 |
| 2-methyl undecene | 8.87 |
| Other alkyl olefins[3] | 9.05 |
| Heavies[4] | 3.53 |
| Total | 99.96 |

[1]Lights include olefins having fewer than 12 carbon atoms.
[2]Linear olefins include $C_{12}$ linear olefins.
[3]Other alkyl olefins include dimethyl, trimethyl, and other $C_{12}$ olefins
[4]Heavies include $C_{12}$ olefin dimers and trimers.

The olefinic feedstock was mixed with benzene to produce a combined feedstock consisting of 93.3 wt-% benzene and 6.7 wt-% olefinic feedstock, which corresponds to a molar ratio of benzene per olefin of about 30:1. A cylindrical reactor, which has an inside diameter of 0.875 in (22.2 mm), was loaded with 75 cc (53.0 g) of the extrudate prepared in Example 8.

The combined feedstock was passed to the reactor and contacted the extrudate at a LHSV of 2.0 $hr^{-1}$, a total pressure of 500 psi(g) (3447 kPa(g)), and a reactor inlet temperature of 125° C. (257° F.). At these conditions, the reactor lined out over a period of 24 hours and then a selective liquid product was collected over the period of the next 6 hours.

The selective liquid product was analyzed by $^{13}C$ nuclear magnetic resonance (NMR) in order to determine the selectivity to 2-phenyl-alkanes and end quaternary phenyl-alkanes. The NMR analytical method typically consists of the following. A 0.5 g sample of phenyl-alkane mixture is diluted to 1.5 g with anhydrous deuterated chloroform. A 0.3 milliliter aliquot of the diluted phenyl-alkane mixture is mixed with 0.3 milliliter of 0.1 M chromium (III) acetylacetonate in deuterated chloroform in a 5 mm NMR tube. A small amount of tetramethylsilane (TMS) is added to the mixture as a 0.0 ppm chemical shift reference. The spectrum is run on a Bruker ACP-300 FT-NMR spectrometer, which is available from Bruker Instruments, Inc., Billerica, Mass., USA. The carbon spectrum is run at a field strength of 7.05 Tesla or 75.469 MHz in a 5 mm QNP probe with a sweep width of 22727 Hz (301.1 ppm) and about 65000 data points are collected. The quantitative carbon spectrum is obtained using gated on-acquisition $^1H$ decoupling (inverse gated decoupling). The quantitative $^{13}C$ spectrum is run with 7.99 microsecond (90°) pulses, 1.442 second acquisition time, a 5 second delay between pulses, a decoupler power, using composite pulse decoupling (CPD), of 18H with a pulse width of 105 microseconds (90°) and at least 2880 scans. The number of scans used depends on whether benzene is stripped from the liquid product prior to taking the above-mentioned 0.5 g sample. The data processing is done with the Bruker PC software WINNMR-1D, Version 6.0, which is also available from Bruker Instruments, Inc. During data processing a line broadening of 1 Hz is applied to the data. Specific peaks are integrated in the region between 152 ppm and 142 ppm. The $^{13}C$ NMR peak identifications of the chemical shifts of the benzylic carbon of the phenyl-alkane isomers is shown in Table 3. As used herein, the term "benzylic carbon" means the carbon in the ring of the phenyl group that is bound to the aliphatic alkyl group.

TABLE 3

$^{13}$C NMR Peak Identifications

| CHEMICAL SHIFT OF THE BENZYLIC CARBON (PPM) | PHENYL-ALKANE ISOMER | TYPE OF QUAT[1] |
|---|---|---|
| 149.6 | 2-methyl-2-phenyl | End |
| 148.3 | 4-methyl-2-phenyl | NQ |
|  | m-methyl-m-phenyl, m > 3 | Internal |
| 148.0 | 5-methyl-2-phenyl | NQ |
| 147.8 | m-methyl-2-phenyl, m > 5 | NQ |
|  | 5-methyl-2-phenyl | NQ |
|  | 2-phenyl (linear) | NQ |
|  | 3-methyl-3-phenyl | Internal |
| 147.6 | 4-methyl-2-phenyl | NQ |
| 147.2 | 3-methyl-2-phenyl | NQ |
| 146.6 | 3-methyl-2-phenyl | NQ |
| 146.2–146.3 | m-methyl-4-phenyl, m ≠ 4 | NQ |
| 145.9–146.2 | m-methyl-3-phenyl, m > 5 | NQ |
| 145.9 | 3-phenyl (linear) | NQ |

NQ = Nonquat

The peak at 148.3 ppm is identified both with 4-methyl-2-phenyl-alkanes and with m-methyl-m-phenyl-alkanes (m>3). However, when the m-methyl-m-phenyl-alkanes (m>3) are present at more than 1%, they are seen as a distinct peak at 0.03 ppm upfield of the peak for the 4-methyl-2-phenyl-alkanes. The peak at 147.8 ppm is considered herein to be identified with the 2-phenyl-alkanes as shown in Table 3, with possible interference from 3-methyl-3-phenyl-alkanes.

The end quaternary phenyl-alkane selectivity is computed by dividing the integral of the peak at 149.6 ppm by the sum of the integrals of all of the peaks listed in Table 3, and multiplying by 100. The 2-phenyl-alkane selectivity can be estimated if the amount of internal quaternary phenyl-alkanes contributing to the peaks at 148.3 ppm and 147.8 ppm is less than about 2%, as determined by the hereinafter-described gas chromatography/mass spectrometry method. As a first approximation, this condition is met when the sum of the integrals of the 4-phenyl-alkane and 3-phenyl-alkane peaks at 146.2–146.3 ppm and 145.9–146.2 ppm (respectively) is small relative to the sum of the integrals of all the peaks from 145.9 ppm to 149.6 ppm and the end quaternary phenyl-alkane selectivity is less than 10. When this is the case, the 2-phenyl-alkane selectivity is computed by dividing the sum of integrals of the peaks from 149.6 to 146.6 ppm by the sum of the integrals of all of the peaks listed in Table 3, and multiplying by 100.

The selective liquid product is also analyzed by gas chromatography/mass spectrometry in order to determine the selectivity to internal quaternary phenyl-alkanes. The gas chromatography/mass spectrometry analytical method typically consists of the following. The selective liquid product is analyzed by an HP 5890 Series II gas chromatograph (GC) equipped with an HP 7673 autosampler and an HP 5972 mass spectrometer (MS) detector. An HP Chemstation was used to control the data acquisition and analysis. The HP 5890 Series II, HP 7673, HP 5972, and HP Chemstation, or suitable equivalent hardware and software, are available from Hewlett Packard Company, Palo Alto, Calif., USA. The GC is equipped with a 30 meter×0.25 mm DB1HT(df=0.1 μm) column or equivalent, which can be obtained from J&W Scientific Incorporated, 91 Blue Ravine Road, Folsom, Calif., USA. Helium carrier gas at 15 psi(g) (103 kPa(g)) and 70° C. (158° F.) is used in constant pressure mode. The injector temperature is held at 275° C. (527° F.). The transfer line and MS source temperatures are held at 250° C. (482° F.). An oven temperature program of 70° C. (158° F.) for 1 minute, then to 180° C. (356° F.) at 1° C. per minute (1.8° F. per minute), then to 275° C. (527° F.) at 10° C. per minute (18° F. per minute), then hold at 275° C. (527° F.) for 5 minutes is used. The MS is tuned by the HP Chemstation software with the software set to standard spectra autotune. The MS detector is scanned from 50–550 Da with a threshold=50.

The concentrations of internal quaternary phenyl-alkanes in the selective liquid product are determined (i.e., the selective liquid product is quantitated) using the method of standard addition. Background information on standard addition methods can be found in Chapter 7 of the book entitled, *Samples and Standards*, by B. W. Woodget et al., published on behalf of ACOL, London by John Wiley and Sons, New York, in 1987.

First, a stock solution of internal quaternary phenyl-alkanes is prepared and quantitated using the following procedure. Benzene is alkylated with a monomethyl alkene using a nonselective catalyst such as aluminum chloride. The nonselective liquid product of this alkylation contains a blend of internal quaternary phenyl-alkanes and is referred to as the stock solution of internal quaternary phenyl-alkanes. Using standard GC methodology, the largest peaks corresponding to internal quaternary phenyl-alkanes in the stock solution are identified, and the concentrations of the internal quaternary phenyl-alkanes in the stock solution are determined (i.e., the stock solution is quantitated) using a flame ionization detector (FID). The retention times of the peaks for the internal quaternary phenyl-alkanes decrease as the index m in the formula m-methyl-m-phenyl-alkane increases and as the number of carbon atoms in the aliphatic alkyl group of the internal quaternary phenyl-alkane decreases. The concentration of each internal quaternary phenyl-alkane is computed by dividing the area of the peak of that internal quaternary phenyl-alkane by the sum of the areas of all of the peaks.

Next, a spiking solution of internal quaternary phenyl-alkanes is prepared in the following manner. An aliquot portion of the stock solution is diluted with dichloromethane (methylene chloride) to attain a nominal concentration of 100 wppm of one particular internal quaternary phenyl-alkane of interest (e.g., 3-methyl-3-phenyl decane). The solution that results is referred to as the spiking solution of internal quaternary phenyl-alkanes. The concentration of any other particular internal quaternary phenyl-alkane in the spiking solution may be greater or less than 100 wppm, depending on the concentration of that internal quaternary phenyl-alkane in the stock solution.

Third, a sample solution is prepared as follows. A weight of 0.05 g of an aliquot portion of the selective liquid product is added to a 10 milliliter volumetric flask. Then the contents of the flask are diluted with dichloromethane by adding dichloromethane up to the 10 milliliter mark. The resulting contents of the flask are referred to as the sample solution.

Fourth, a resultant solution is prepared in the following manner. A weight of 0.05 g of an aliquot portion of the selective liquid product is added to a 10 milliliter volumetric flask. The spiking solution is then added to the flask up to the 10 milliliter mark to dilute the contents. The resulting contents of the flask are referred to as the resultant solution.

Both the sample solution and the resultant solution are analyzed by GC/MS using the above-described conditions.

Table 4 lists the ions that were extracted from the full MS scan, plotted, and integrated using the HP Chemstation software. The HP Chemstation software is used to determine the individual extracted ion peak areas that correspond to the internal quats listed in Table 4.

TABLE 4

RATIO OF MASS TO CHARGE OF ION FOR PEAKS OF EXTRACTED IONS

| INTERNAL QUATERNARY PHENYL-ALKANE | NUMBER OF CARBON ATOMS IN ALIPHATIC ALKYL GROUP OF THE INTERNAL QUATERNARY PHENYL-ALKANE | RATIO OF MASS TO CHARGE (M/Z) OF TWO EXTRACTED IONS CORRESPONDING TO INTERNAL QUATERNARY PHENYL-ALKANE |
|---|---|---|
| 3-methyl-3-phenyl | 11 | 133 and 203 |
|  | 12 | 133 and 217 |
|  | 13 | 133 and 231 |
| 4-methyl-4-phenyl | 11 | 147 and 189 |
|  | 12 | 147 and 203 |
|  | 13 | 147 and 217 |
| 5-methyl-5-phenyl | 11 | 161 and 175 |
|  | 12 | 161 and 189 |
|  | 13 | 161 and 203 |

The concentration of each internal quaternary phenyl-alkane in Table 4 is computed using the following formula:

$$C = S\left(\frac{A_1}{A_2 - A_1}\right)$$

where

C=concentration of internal quaternary phenyl-alkane in sample solution, wt-%

S=concentration of internal quaternary phenyl-alkane in spiking solution, wt-%

$A_1$=peak area of internal quaternary phenyl-alkane in sample solution, area units $A_2$=peak area of internal quaternary phenyl-alkane in resultant solution, area units The concentrations C and S have the same units, provided that the areas $A_1$ and $A_2$ have the same units. Then, the concentration of each internal quaternary phenyl-alkane in the selective liquid product is computed from the concentration of that internal quaternary phenyl-alkane in the sample solution by accounting for the dilution effect of the dichloromethane in the sample solution. In this manner, the concentration in the selective liquid product of each of the internal quaternary phenyl-alkanes in Table 4 is computed. The total concentration of internal quaternary phenyl-alkanes in the selective liquid product, $C_{IQPA}$, is computed by summing the individual concentrations of each of the internal quaternary phenyl-alkanes in Table 4.

It should be pointed out that the selective liquid product may contain internal quaternary phenyl-alkanes other than those listed in Table 4, such as m-methyl-m-phenyl-alkanes where m>5, depending on the number of carbon atoms in the aliphatic alkyl groups of the phenyl-alkanes. It is believed that, with the $C_{12}$ olefinic feedstock and the conditions of this Example 9, the concentrations of such other internal quaternary phenyl-alkanes are relatively low compared to those of the internal quaternary phenyl-alkanes listed in Table 4. Therefore, for purposes of this Example 9, the total concentration of internal quaternary phenyl-alkanes in the selective liquid product, $C_{IQPA}$, is computed by summing only the individual concentrations of each of the internal quaternary phenyl-alkanes in Table 4. However, if the olefinic feedstock had comprised olefins having, say, up to 28 carbon atoms, then the total concentration of internal quaternary phenyl-alkanes in the selective liquid product, $C_{IQPA}$, would be computed by summing individual concentrations of m-methyl-m-phenyl-alkanes, where m is from 3 to 13. In more general terms, if the olefinic feedstock contains olefins having x carbon atoms, then the total concentration of internal quaternary phenyl-alkanes in the selective liquid product, $C_{IPQA}$, is computed by summing individual concentrations of m-methyl-m-phenyl-alkanes where m is from 3 to x/2. A person of ordinary skill in the art of gas chromatography/mass spectrometry can, without undue experimentation, identify at least one peak with a ratio of mass to charge (m/z) of an extracted ion corresponding to each internal quaternary phenyl-alkane, so that the concentration of all internal quaternary phenyl-alkanes may be determined and then summed to arrive at $C_{IQPA}$.

The selectivity to internal quaternary phenyl-alkanes in the selective liquid product is computed using the following formula:

$$Q = 100\left(\frac{C_{IQPA}}{C_{MAB}}\right)$$

where

Q=selectivity to internal quaternary phenyl-alkanes $C_{IQPA}$=concentration of internal quaternary phenyl-alkanes in selective liquid product, wt-%

$C_{MAB}$=concentration of modified alkylbenzenes in selective liquid product, wt-%

The concentration of modified alkylbenzenes, $C_{MAB}$, in the selective liquid product is determined in the following manner. First, the concentration of impurities in the selective liquid product is determined by a gas chromatography method. As used in this context of determining $C_{MAB}$, the term "impurities" means components of the selective liquid product that lie outside a specific retention time range that is used in the gas chromatography method. "Impurities", generally includes benzene, some dialkylbenzenes, olefins, paraffins, etc.

To determine the amount of impurities from the selective liquid product, the following gas chromatography method is used. The scope of the invention as set forth in the claims is not limited to determining the amount of impurities by use of only the specific equipment, specific sample preparation, and specific GC parameters described below. Equivalent equipment, equivalent sample preparation, and equivalent GC parameters that are different but that produce equivalent results to those described below may also be used to determine the amount of impurities in the selective liquid product.

Equipment:.

Hewlett Packard Gas Chromatograph HP 5890 Series II equipped with a split/splitless injector and flame-ionization detector (FID)

J&W Scientific capillary column DB-1HT, 30 meter length, 0.25 mm inside diameter, 0.1 micro-meter film thickness, catalog no. 1221131.

Restek Red lite Septa 11 mm, catalog no. 22306. (Available from Restek Corporation, 110 Benner Circle, Bellefonte, Pa., USA).

Restek 4 mm Gooseneck inlet sleeve with a carbofrit, catalog no. 20799-209.5.

O-ring for inlet liner Hewlett Packard, catalog no. 51804182.

J. T. Baker HPLC grade methylene chloride, catalog no. 9315-33, or equivalent. (Available from J. T. Baker Co., 222 Red School Lane, Phillipsburg, N.J., USA).

2 ml gas chromatograph autosampler vials with crimp tops, or equivalent.

Sample Preparation:

Weigh 4–5 mg of sample into a 2 ml GC autosampler vial.

Add 1 ml methylene chloride to the GC vial; seal with 11 mm crimp vial Teflon lined closures (caps), HP part no. 5181-1210 (available from Hewlett Packard Company), using crimper tool, HP part no. 8710-0979 (available from Hewlett Packard Company); and mix well.

The sample is now ready for injection into the GC.

GC Parameters:

Carrier gas: hydrogen.

Column head pressure: 9 psi.

Flows: column flow, 1 ml/min; split vent, about 3 ml/min; septum purge, 1 ml/min.

Injection: HP 7673 Autosampler, 10 microliter syringe, 1 microliter injection.

Injector temperature: 350° C. (662° F.)

Detector temperature: 400° C. (752° F.)

Oven temperature program: initial hold at 70° C. (158° F.) for 1 minute;

heating rate of 1° C. per minute (1.8° F. per minute); final hold at 180° C. (356° F.) for 10 minutes.

Two standards that have been freshly distilled to a purity of more than 98 mol-% are required for this gas chromatography method. In general, each standard is a 2-phenyl-alkane. One of the 2-phenyl-alkane standards, which is referred to hereinafter as the light standard, has at least one fewer carbon atom in its aliphatic alkyl group than that of the olefin in the olefinic feedstock charged to the alkylation zone that has the fewest number of carbon atoms. The other 2-phenyl-alkane standard, which is referred to hereinafter as the heavy standard, has at least one more carbon atom in its aliphatic alkyl group than that of the olefin in the olefinic feedstock charged to the alkylation zone that has the most number of carbon atoms. For example, if the olefins in the olefinic feedstock that is charged to the alkylation zone have from 10 to 14 carbon atoms, then the suitable standards include 2-phenyl-octane as the light standard and 2-phenyl-pentadecane as the heavy standard.

Each standard is subjected to the gas chromatography method using the conditions specified above to determine its retention time, and the two standard retention times in turn define a retention time range. Then, an aliquot sample of the selective liquid product is analyzed by the gas chromatography method using the above conditions. If more than about 90% of the total GC area is within the retention time range, then the impurities in the selective liquid product are deemed to be not more than about 10 wt-% of the selective liquid product, and, for the sole purpose of computing the selectivity to internal quaternary phenyl-alkanes, $C_{MAB}$ is assumed to be 100 wt-%.

On the other hand, if the percent of the total GC area within the retention time range is not more than about 90%, then the impurities in the selective liquid product are deemed to be more than about 10 wt-% of the selective liquid product. In this case, in order to determine $C_{MAB}$, impurities are removed from the selective liquid product, and the following distillation method is used. However, the scope of the invention as set forth in the claims is not limited to removing impurities from the selective liquid product using only the specific equipment, specific sample preparation, and specific distillation conditions described below. Equivalent equipment, equivalent procedures, and equivalent distillation conditions that are different but that produce equivalent results to those described below may also be used to remove impurities in the selective liquid product.

The distillation method to remove impurities from the selective liquid product is as follows. A 5-liter, 3-necked round bottom flask with 24/40, joints is equipped with a magnetic stir bar. A few boiling chips are added to the flask. A 9-½ inch (24.1 cm) long Vigreux condenser with a 24/40 joint is placed in the center neck of the flask. A water cooled condenser is attached to the top of the Vigreux condenser which is fitted with a calibrated thermometer; A vacuum receiving flask is attached to the end of the condenser. A glass stopper is placed in one side arm of the 5-liter flask and a calibrated thermometer is placed in the other side arm. The flask and the Vigreux condenser are wrapped with aluminum foil. To the 5-liter flask is added a weight of 2200 to 2300 g of an aliquot portion of the selective liquid product which contains about 10 wt-% or more of impurities, as determined by the above gas chromatography method. A vacuum line leading from a vacuum pump is attached to the receiving flask. The selective liquid product in the 5-liter flask is stirred, and vacuum is applied to the system. Once the maximum vacuum is reached (at least 1 inch (25.4 mm) Hg by gauge or less), the selective liquid product is heated by means of an electric heating mantle.

After the heating begins, the distillate is collected in two fractions. One fraction, which is referred to hereinafter as fraction A, is collected from about 25° C. (77° F.) to about the temperature of the boiling point of the light standard at the pressure at the top of the Vigreux condenser, as measured by the calibrated thermometer at the top of the Vigreux condenser. The other fraction, fraction B, is collected from about the temperature of the boiling point of the light standard at the pressure at the top of the Vigreux condenser to about the temperature of the boiling point of the heavy standard at the pressure at the top of the Vigreux condenser, as measured by the calibrated thermometer at the top of the Vigreux condenser. Low-boiling fraction A and high-boiling pot residues are discarded. Fraction B contains the modified alkylbenzenes of interest, and is weighed. A person of ordinary skill in the art of distillation can scale this method as needed. Vapor pressures for phenyl-alkanes at various temperatures can be determined from the article written by Samuel B. Lippincott and Margaret M. Lyman, published in Industrial and Engineering Chemistry, Vol. 38, in 1946, and starting at page 320. Using the Lippincott et al. article and without undue experimentation, a person of ordinary skill in the art can determine appropriate temperatures for collecting fractions A and B.

Next, an aliquot sample of fraction B is analyzed by the gas chromatography method using the above conditions. If more than about 90% of the total GC area for fraction B is within the retention time range, then the impurities in fraction B are deemed to be not more than about 10 wt-% of the selective liquid product, and, for the sole purpose of computing the selectivity to internal quaternary phenyl-alkanes, $C_{MAB}$ is computed by dividing the weight of fraction B collected by the weight of the aliquot portion of the selective liquid product charged to the 5-liter flask in the above distillation method. On the other hand, if the percent of the total GC area for fraction B within the retention time range is not more than about 90%, then the impurities in fraction B are deemed to be more than about 10 wt-% of fraction B. In this case, impurities are removed from fraction B by again using the above distillation method. Accordingly, a low-boiling fraction (which is referred to as fraction C), high-boiling pot residues are discarded, a fraction (which is referred to herein as fraction D) containing the modified alkylbenzenes of interest is recovered and weighed, and an aliquot sample of fraction D is analyzed by the gas chromatography method. If more than about 90% of the total GC area for fraction D is within the retention time range, then for the sole purpose of computing the selectivity to internal quaternary phenyl-alkanes, $C_{MAB}$ is computed by dividing the weight of fraction D by the weight of the aliquot portion of the selective liquid product originally charged to the 5-liter flask. Otherwise, the distillation and gas chromatography methods are repeated for fraction D.

A person of ordinary skill in the art of distillation and gas chromatography will appreciate that the above-described distillation and gas chromatography methods can be repeated until a fraction containing the modified alkylbenzenes of interest and having less than 10 wt-% impurities is collected, provided that sufficient quantity of material remains after each distillation for further testing by these methods. Then, once $C_{MAB}$ is determined, the selectivity to internal quaternary phenyl-alkanes, Q, is computed using the above formula.

The results of these analyses are shown in the Table 5:

TABLE 5

| Liquid Product Analysis | | |
| --- | --- | --- |
| 2-Phenyl-Alkane Selectivity | End Quaternary Phenyl-Alkane Selectivity | Internal Quaternary Phenyl-Alkane Selectivity |
| 82.0% | 6.98% | 1.9% |

In the absence of shape selectivity, such as if an alkylation catalyst such as aluminum chloride or HF were used, most of the 2-methyl undecene would be expected to form 2-methyl-2-phenyl undecane (that is, an end quat). Likewise, most of the 6-methyl undecene, 5-methyl undecene, 4-methyl undecene, and 3-methyl undecene would be expected to form internal quats. The linear olefins would be expected to produce a statistical distribution of 2-phenyl-dodecane, 3-phenyl-dodecane, 4-phenyl-dodecane, 5-phenyl-dodecane, and 6-phenyl-dodecane. Thus, if the lights, the heavies, and the other alkyl olefins listed in Table 1 are excluded from the computations, the 2-phenyl-alkane selectivity would be no greater than 17 and the internal quaternary phenyl-alkane selectivity would approach 55. The Table shows that the 2-phenyl-alkane selectivity is significantly higher than expected in the absence of shape selectivity and that the internal quaternary alkylbenzene selectivity obtained using the mordenite catalyst is much less than the internal quaternary alkylbenzene selectivity that would be expected in the absence of shape selectivity.

What is claimed is:

1. A modified alkylbenzene composition, wherein the modified alkylbenzene is produced by a process comprising the steps of:
    a) passing a feed stream containing $C_8$–$C_{28}$ paraffins to an isomerization zone, operating the isomerization zone at isomerization conditions sufficient to isomerize paraffins, and recovering from the isomerization zone an isomerized product stream comprising paraffins;
    b) passing at least a portion of the isomerized product stream to a dehydrogenation zone, operating the dehydrogenation zone at dehydrogenation conditions sufficient to dehydrogenate paraffins, and recovering from the dehydrogenation zone a dehydrogenated product stream comprising monoolefins and paraffins, wherein the monoolefins in the dehydrogenated product stream have from about 8 to about 28 carbon atoms, and wherein at least a portion of. the monoolefins in the dehydrogenated product stream have 3 or 4 primary carbon atoms and no quaternary carbon atoms;
    c) passing an aryl compound and at least a portion of the dehydrogenated product stream comprising monoolefins to an alkylation zone, operating the alkylation zone at alkylation conditions sufficient to alkylate the aryl compound with monoolefins in the presence of an alkylation catalyst to form arylalkanes comprising molecules having one aryl portion and one aliphatic alkyl portion containing from about 8 to about 28 carbon atoms; wherein at least a portion of the arylalkanes formed in the alkylation zone have 2, 3, or 4 primary carbon atoms and no quaternary carbon atoms except for any quaternary carbon atom bonded by a carbon-carbon bond with a carbon atom of the aryl portion; and wherein the alkylation has a selectivity to 2-phenyl-alkanes of from 40 to 100 and a selectivity to internal quaternary phenyl-alkanes of less than 10;
    d) recovering from the alkylation zone an alkylate product stream comprising arylalkanes and a recycle stream comprising paraffins; and
    e) passing at least a portion of the recycle stream to the isomerization zone or the dehydrogenation zone.

2. The composition of claim 1 further characterized in that at least one of the at least a portion of the isomerized product stream, the at least a portion of the dehydrogenated product stream, and the at least a portion of the recycle stream comprises paraffins having from about 8 to about 28 carbon atoms.

3. The composition of claim 2 further characterized in that at least a portion of the paraffins in at least one of the at least a portion of the isomerized product stream, the at least a portion of the dehydrogenated product stream, and the at least a portion of the recycle stream have 3 or 4 primary carbon atoms and no quaternary carbon atoms.

4. The composition of claim 3 further characterized in that the at least a portion of the isomerized product stream has a concentration of paraffins having 3 or 4 primary carbon atoms and no quaternary carbon atoms of greater than about 25 mol-% of the at least a portion of the isomerized product stream.

5. The composition of claim 2 further characterized in that at least a portion of the paraffins in at least one of the at least a portion of the isomerized product stream, the at least a portion of the dehydrogenated product stream, and the at least a portion of the recycle stream have secondary carbon atoms and 2 primary carbon atoms.

6. The composition of claim 5 further characterized in that the at least a portion of the isomerized product stream has a concentration of paraffins having secondary carbon atoms and 2 primary carbon atoms of less than about 75 mol-% of the at least a portion of the isomerized product stream.

7. The composition of claim 2 further characterized in that at least a portion of the paraffins in at least one of the at least a portion of the isomerized product stream, the at least a portion of the dehydrogenated product stream, and the at least a portion of the recycle stream comprise at least one quaternary carbon atom.

8. The composition of claim 7 further characterized in that the at least a portion of the isomerized product stream has a concentration of paraffins having at least one quaternary carbon atom of less than about 10 mol-% of the at least a portion of the isomerized product stream.

9. The composition of claim 1 further characterized in that the isomerization zone contains an isomerization catalyst comprising a Group VIII (IUPAC 8-10) metal and a support material selected from the group consisting of amorphous alumina, amorphous silica-alumina, ferrierite, ALPO-31, SAPO-11, SAPO-31, SAPO-37, SAPO-41, SM-3, and MgAPSO-31.

10. The composition of claim 1 further characterized in that the isomerization zone operates at isomerization conditions comprising a temperature of from about 50 to about 400° C. and a molar ratio of hydrogen per hydrocarbon of greaterthan 0.01:1.

11. The composition of claim 1 further characterized in that the dehydrogenation zone contains a dehydrogenation catalyst comprising at least one Group VIII (IUPAC 8-10) metal, a promoter metal, a modifier metal, and a refractory inorganic oxide.

12. The composition of claim 11 further characterized in that the dehydrogenation catalyst comprises an inner core and an outer layer bonded to the inner core, the outer layer comprising an outer refractory inorganic oxide having uniformly dispersed thereon the at least one Group VIII (IUPAC 8-10) metal and the promoter metal, and the dehydrogenation catalyst further having dispersed thereon the modifier metal.

13. The composition of claim 12 further characterized in that the dehydrogenation catalyst has the outer layer bonded to the inner core to the extent that the attrition loss is less than 10 wt-% based on the weight of the outer layer.

14. The composition of claim 1 further characterized in that the dehydrogenation zone operates at dehydrogenation conditions comprising a temperature of from about 400 to about 525° C. and a pressure of less than 345 kPa(g).

15. The composition of claim 1 further characterized in that the alkylation catalyst comprises a zeolite having a zeolite structure type selected from the group consisting of BEA, MOR, MTW, and NES.

16. The composition of claim 15 wherein the zeolite structure type comprises MOR.

17. The composition of claim 1 further characterized in that the alkylation conditions comprise a temperature of from about 80 to about 200° C. and a pressure sufficient to maintain a liquid phase or supercritical conditions.

18. The composition of claim 1 wherein the aryl compound comprises a compound selected from the group consisting of benzene, toluene, and ethylbenzene.

19. The composition of claim 1 wherein the monoolefins have from 10 to 15 carbon atoms.

20. The composition of claim 1 wherein the aliphatic alkyl portion has from 10 to 15 carbon atoms.

21. The composition of claim 1 wherein the monoolefins comprise monomethyl-alkenes.

22. The composition of claim 1 wherein the arylalkanes comprise monomethyl-phenyl-alkanes.

23. The composition of claim 1 further characterized in that the at least a portion of the recycle stream has a concentration of monoolefins of less than 0.3 wt-%.

24. The composition of claim 1 further characterized in that the dehydrogenated product stream has a first concentration of diolefins, at least a portion of the dehydrogenated product stream passes to a selective diolefin hydrogenation zone, a selective diolefin hydrogenation product stream having a second concentration of diolefins that is less than the first concentration of diolefins is recovered from the selective diolefin hydrogenation zone, and at least a portion of the selective diolefin hydrogenation product stream passes to the alkylation zone.

25. The composition of claim 24 further characterized in that the selective diolefin hydrogenation product stream has a first concentration of aromatic by-products, at least a portion of the selective diolefin hydrogenation product stream passes to an aromatics removal zone, an aromatics removal product stream having a second concentration of aromatic by-products that is less than the first concentration of aromatic by-products is recovered from the aromatics removal zone, and at least a portion of the aromatics removal product stream passes to the alkylation zone.

26. The composition of claim 1 further characterized in that the dehydrogenated product stream has a first concentration of aromatic by-products, at least a portion of the dehydrogenated product stream passes to an aromatics removal zone, an aromatics removal product stream having a second concentration of aromatic by-products that is less than the first concentration of aromatic by-products is recovered from the aromatics removal zone, and at least a portion of the aromatics removal product stream passes to the alkylation zone.

27. The composition of claim 1 wherein at least a portion of the recycle stream passes to the isomerization zone.

28. The composition of claim 27 further characterized in that the isomerization zone contains a first bed containing isomerization catalyst and a second bed containing isomerization catalyst, the feed stream passes to the first bed operating at first bed conditions to isomerize paraffins, a first bed effluent comprising paraffins is withdrawn from the first bed, at least a portion of the first bed effluent and the at least a portion of the recycle stream passes to the second bed operating at second bed conditions to isomerize paraffins, and the isomerized product stream is recovered from the second bed.

29. The composition of claim 1 wherein at least a portion of the recycle stream passes to the dehydrogenation zone.

30. The composition of claim 29 further characterized in that the dehydrogenation zone contains a first bed containing dehydrogenation catalyst and a second bed containing dehydrogenation catalyst, the at least a portion of the isomerized product stream passes to the first bed operating at first bed conditions to dehydrogenate paraffins, a first bed effluent comprising paraffins is withdrawn from the first bed, at least a portion of the first bed effluent and the at least a portion of the recycle stream passes to the second bed operating at second bed conditions to dehydrogenate paraffins, and the dehydrogenated product stream is recovered from the second bed.

31. The composition of claim 1 wherein at least a portion of the isomerized product stream comprises paraffins having from about 8 to about 28 total carbon atoms, 3 or 4 primary carbon atoms, and no quaternary carbon atoms.

32. A modified alkylbenzene composition, wherein the modified alkylbenzene is produced by a process comprising the steps of:
   a) passing a feed stream containing paraffins to an isomerization zone, operating the isomerization zone at isomerization conditions sufficient to isomerize paraffins, and recovering from the isomerization zone an isomerized product stream comprising paraffins;
   b) passing at least a portion of the isomerized product stream to a dehydrogenation zone, operating the dehydrogenation zone at dehydrogenation conditions sufficient to dehydrogenate paraffins, and recovering from the dehydrogenation zone a dehydrogenated product stream comprising monoolefins and paraffins;

c) passing an aryl compound and at least a portion of the dehydrogenated product stream comprising monoolefins to an alkylation zone, operating the alkylation zone at alkylation conditions sufficient to alkylate the aryl compound with monoolefins in the presence of an alkylation catalyst to form arylalkanes comprising molecules having one aryl group and one aliphatic alkyl group, wherein the arylalkanes have:

(i) an average weight of the aliphatic alkyl groups of the arylalkanes of between the weight of a $C_{10}$ aliphatic alkyl group and a $C_{13}$ aliphatic alkyl group;

(ii) a content of arylalkanes having the phenyl group attached to the 2- and/or 3-position of the aliphatic alkyl group of greater than 55 wt-% of the arylalkanes; and (iii) an average level of branching of the aliphatic alkyl groups of the arylalkanes of from 0.25 to 1.4 alkyl group branches per arylalkane molecule when the sum of the contents of 2-phenyl-alkanes and 3-phenyl-alkanes is more than 55 wt-% and less than or equal to 85 wt-% of the arylalkanes, or an average level of branching of the aliphatic alkyl groups of the arylalkanes of from 0.4 to 2.0 alkyl group branches per arylalkane molecule when the sum of the concentrations of 2-phenyl-alkanes and the 3-phenyl-alkanes is greater than 85 wt-% of the arylalkanes; and wherein the aliphatic alkyl groups of the arylalkanes comprise linear aliphatic alkyl groups, mono-branched aliphatic alkyl groups, or di-branched aliphatic alkyl groups, and wherein the alkyl group branches if any on the aliphatic alkyl chain of the aliphatic alkyl groups comprise methyl group branches, ethyl group branches, or propyl group branches, and wherein the alkyl group branches if any attach to any position on the aliphatic alkyl chain of the aliphatic alkyl groups provided that arylalkanes having at least one quaternary carbon atom on the aliphatic alkyl group comprise less than 20% of the arylalkanes;

d) recovering from the alkylation zone an alkylate product stream comprising arylalkanes and a recycle stream comprising paraffins; and e) passing at least a portion of the recycle stream to the isomerization zone or the dehydrogenation zone.

* * * * *